(12) United States Patent
Sauer

(10) Patent No.: US 10,231,723 B2
(45) Date of Patent: Mar. 19, 2019

(54) SURGICAL RIB CUTTER AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 444 days.

(21) Appl. No.: 14/683,829

(22) Filed: Apr. 10, 2015

(65) Prior Publication Data

US 2016/0166263 A1 Jun. 16, 2016

Related U.S. Application Data

(60) Provisional application No. 62/092,222, filed on Dec. 15, 2014.

(51) Int. Cl.
| | |
|---|---|
| *A61B 17/16* | (2006.01) |
| *A61B 17/02* | (2006.01) |
| *A61B 17/04* | (2006.01) |
| *A61B 17/00* | (2006.01) |
| *A61B 17/34* | (2006.01) |

(52) U.S. Cl.
CPC ...... *A61B 17/0206* (2013.01); *A61B 17/0469* (2013.01); *A61B 17/0482* (2013.01); *A61B 2017/00685* (2013.01); *A61B 2017/00862* (2013.01); *A61B 2017/0237* (2013.01); *A61B 2017/3427* (2013.01)

(58) Field of Classification Search
CPC ............ A61B 17/1606; A61B 17/1608; A61B 17/1611; A61B 17/1693
See application file for complete search history.

(56) References Cited

U.S. PATENT DOCUMENTS

| | | | |
|---|---|---|---|
| 2,362,957 A | 11/1944 | Hackett | |
| 4,852,552 A | 8/1989 | Chaux | |
| 5,676,636 A | 10/1997 | Chin | |
| 6,159,231 A | 12/2000 | Looney | |
| 2003/0060686 A1 | 3/2003 | Taylor | |
| 2014/0155901 A1* | 6/2014 | Jacobs | ............... A61B 17/1608 606/82 |
| 2016/0166244 A1 | 6/2016 | Sauer | |
| 2016/0166263 A1 | 6/2016 | Sauer | |

OTHER PUBLICATIONS

Oct. 19, 2017 International Search Report; Bai, Lingfei , International Preliminary Report on Patentability for PCT/US2016/026603.

* cited by examiner

*Primary Examiner* — Olivia C Chang
(74) *Attorney, Agent, or Firm* — David J. Gervasi; Christopher B. Miller

(57) ABSTRACT

A surgical rib cutter is disclosed. The surgical rib cutter includes a housing defining one or more guide slots. The surgical rib cutter also includes an anterior arm unit comprising an anterior effector configured to interact with an anterior side of a rib. The surgical rib cutter further includes a posterior arm unit comprising a posterior effector configured to interact with a posterior side of said rib. The surgical rib cutter also has an actuator movable relative to the housing and operationally coupled to at least one of the anterior and posterior arm units to move said at least one of the anterior and posterior arm units within at least one of the one or more guide slots to create a relative movement between the anterior and posterior arm units, said relative movement causing one of the anterior effector or the posterior effector to create a green stick break in said rib.

14 Claims, 23 Drawing Sheets

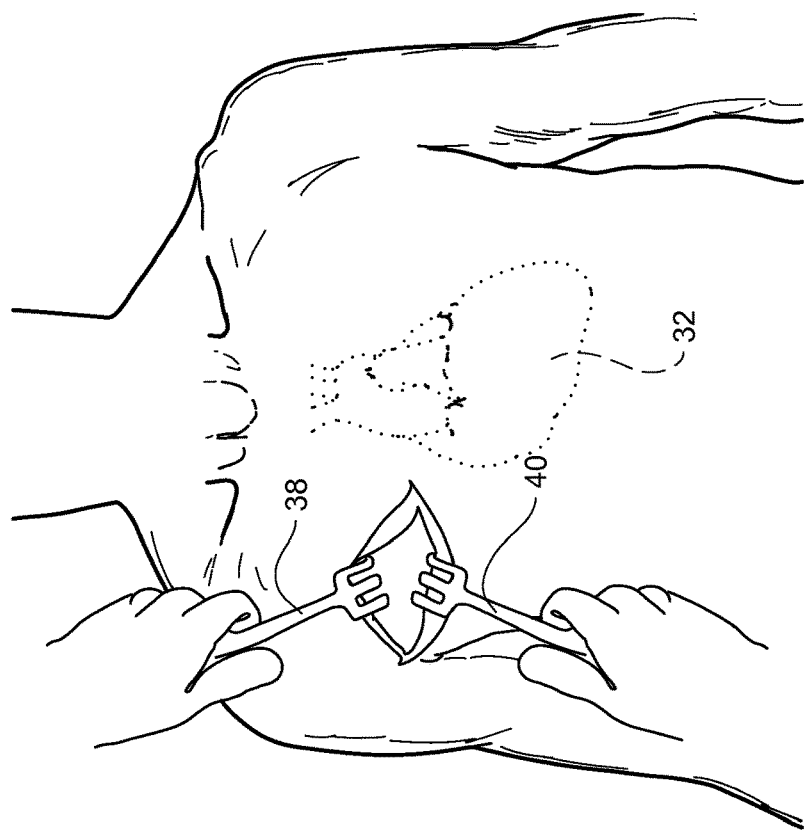
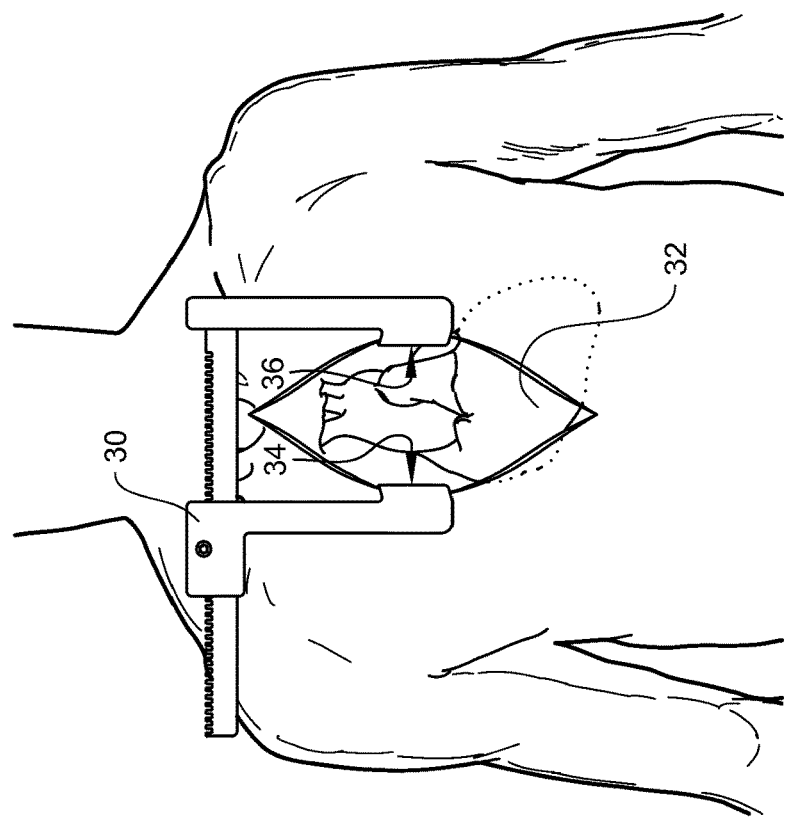
FIG. 1A
(PRIOR ART)
FIG. 1B
(PRIOR ART)

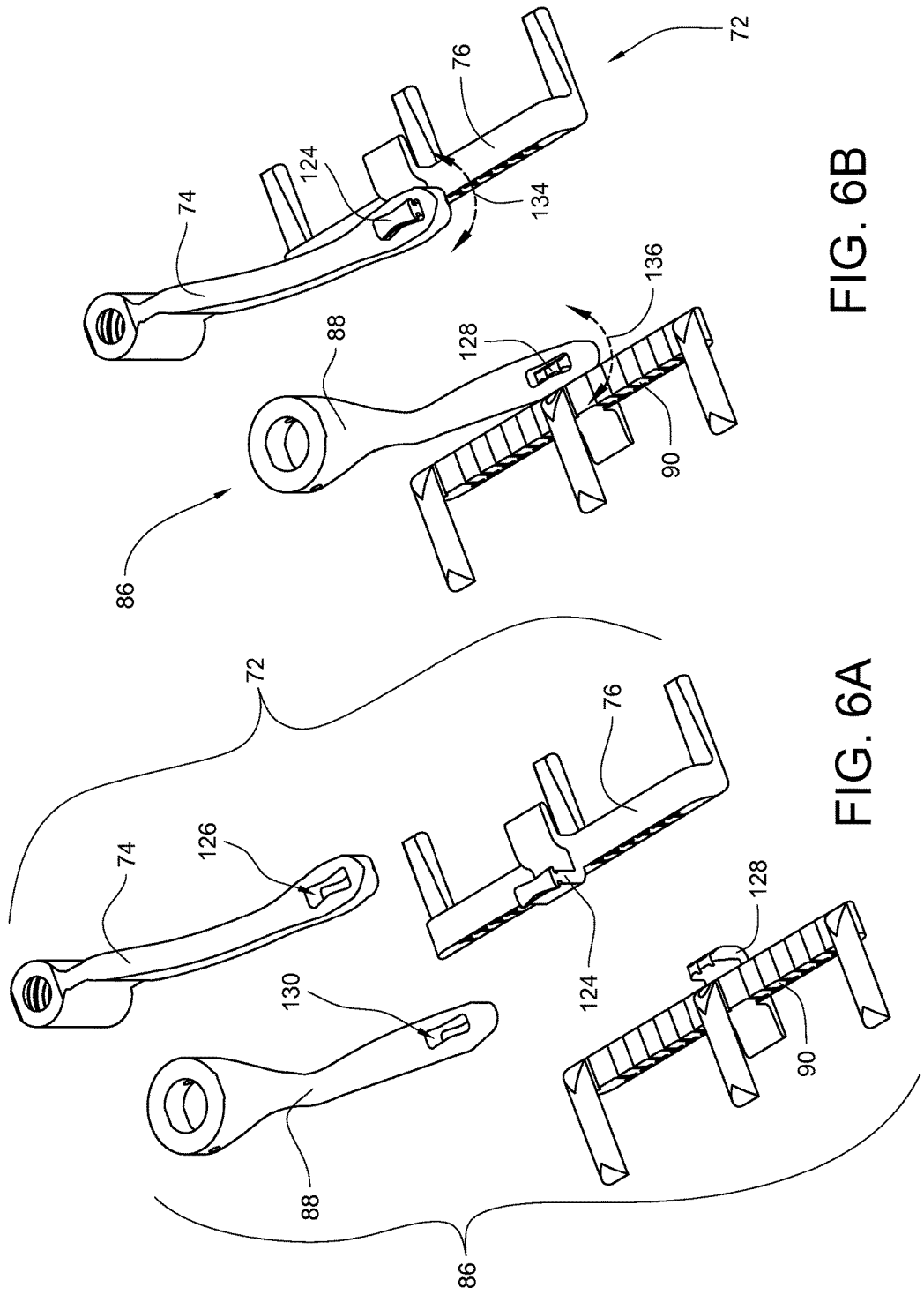

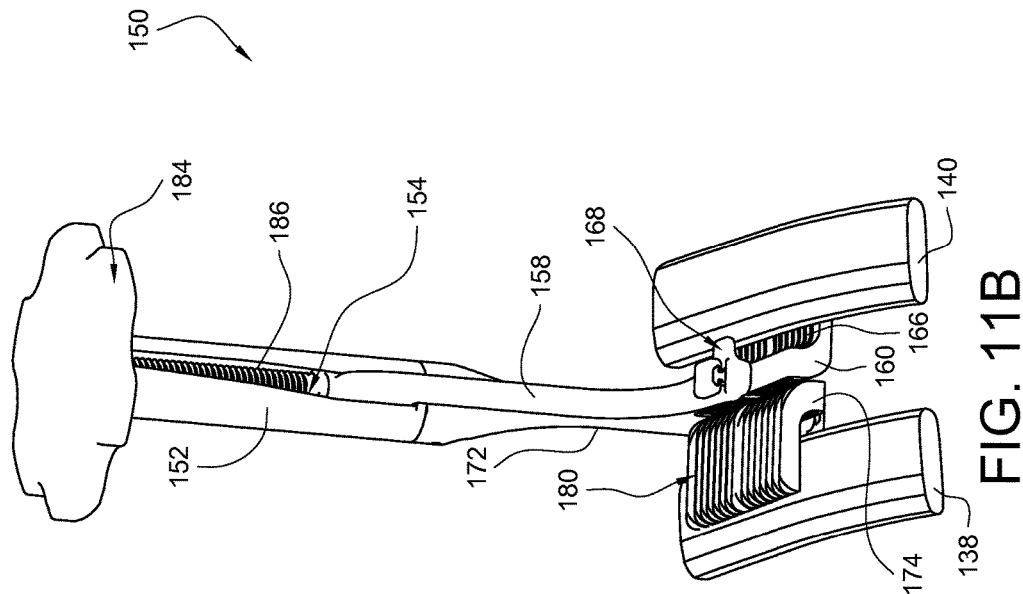
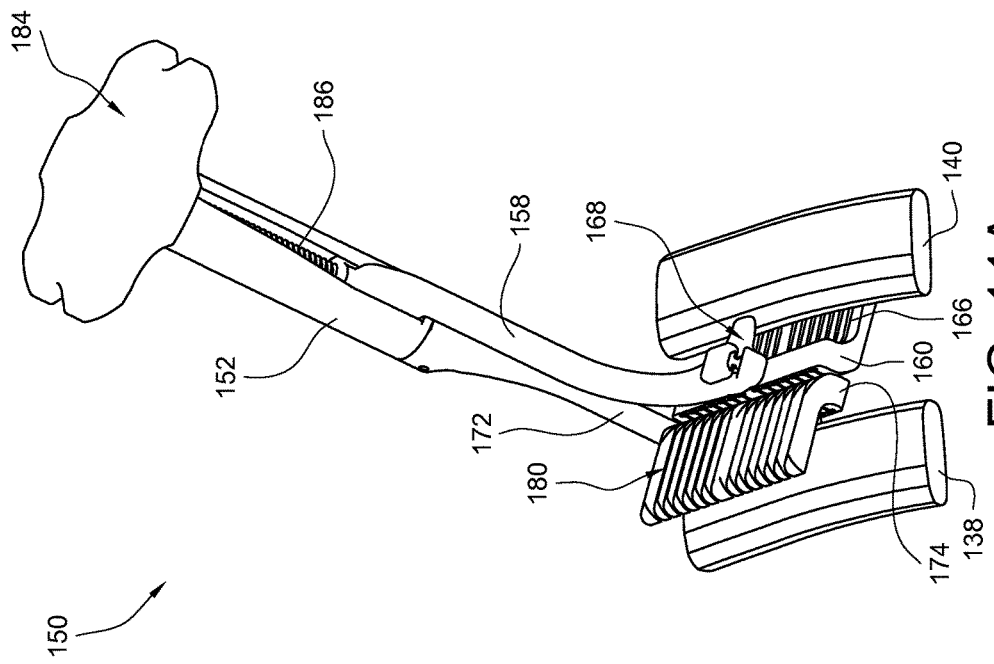
FIG. 11A
FIG. 11B

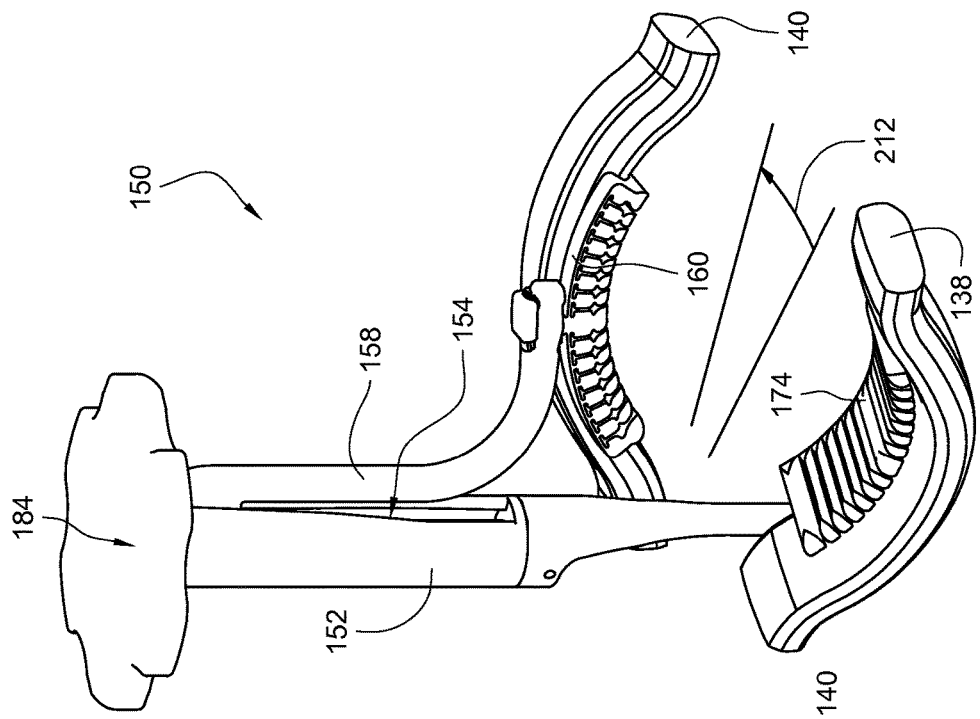
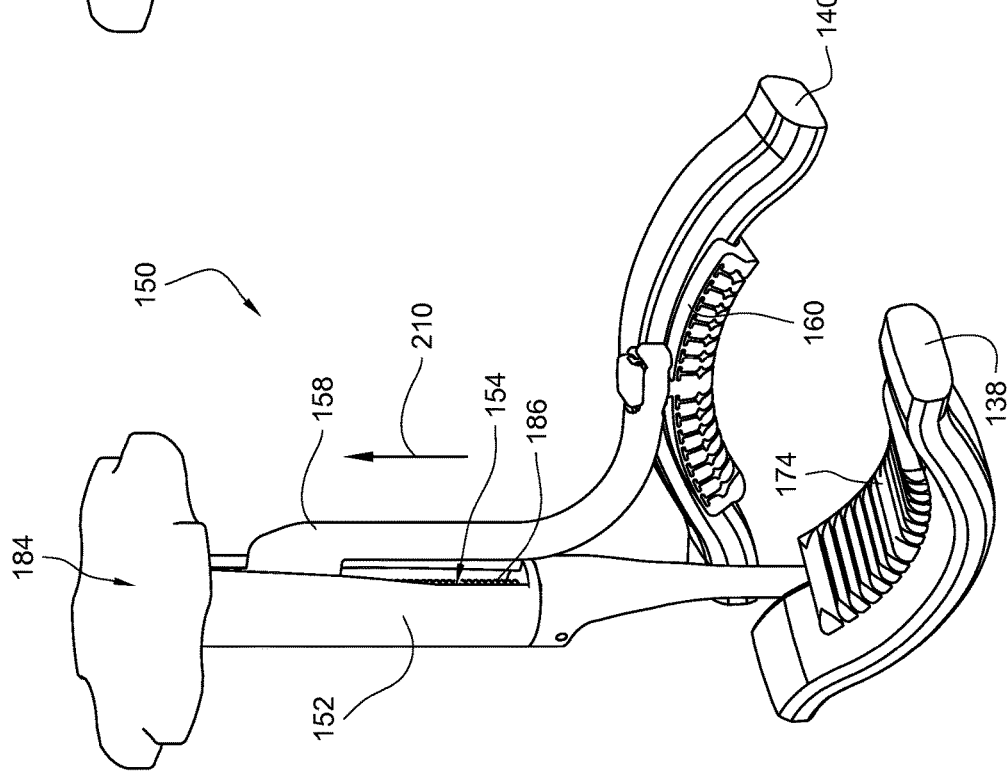

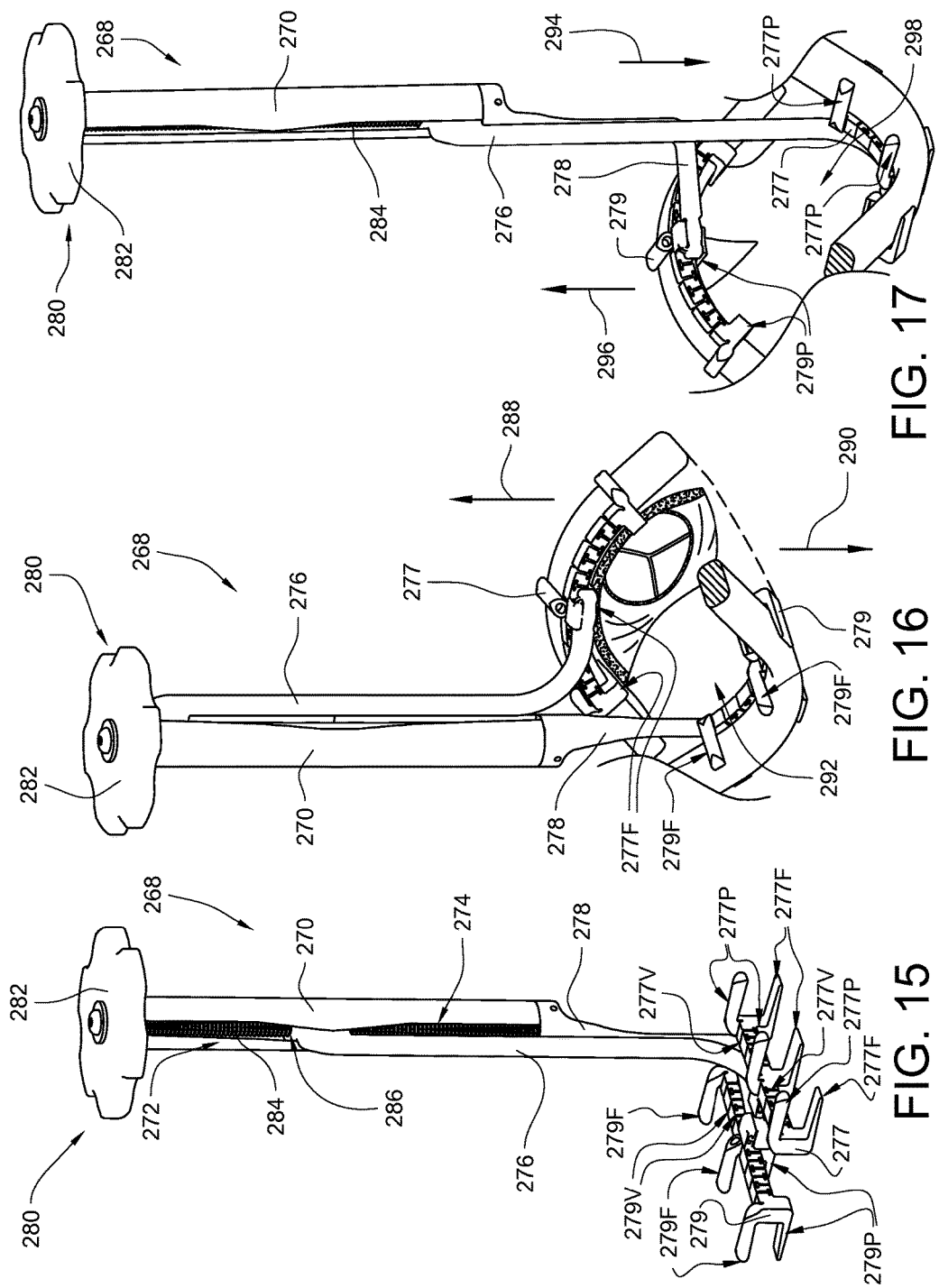

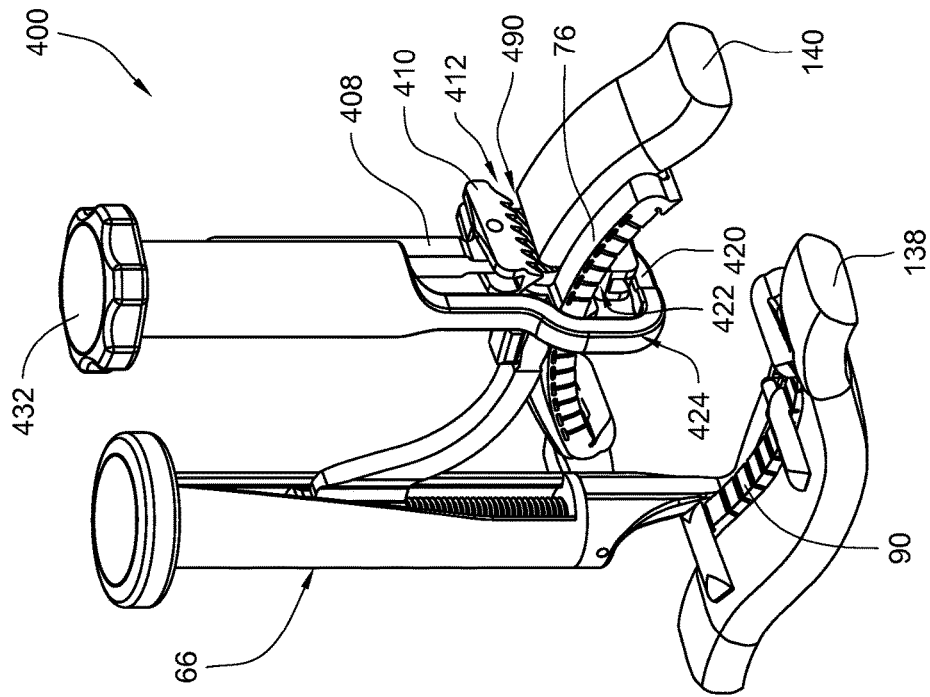
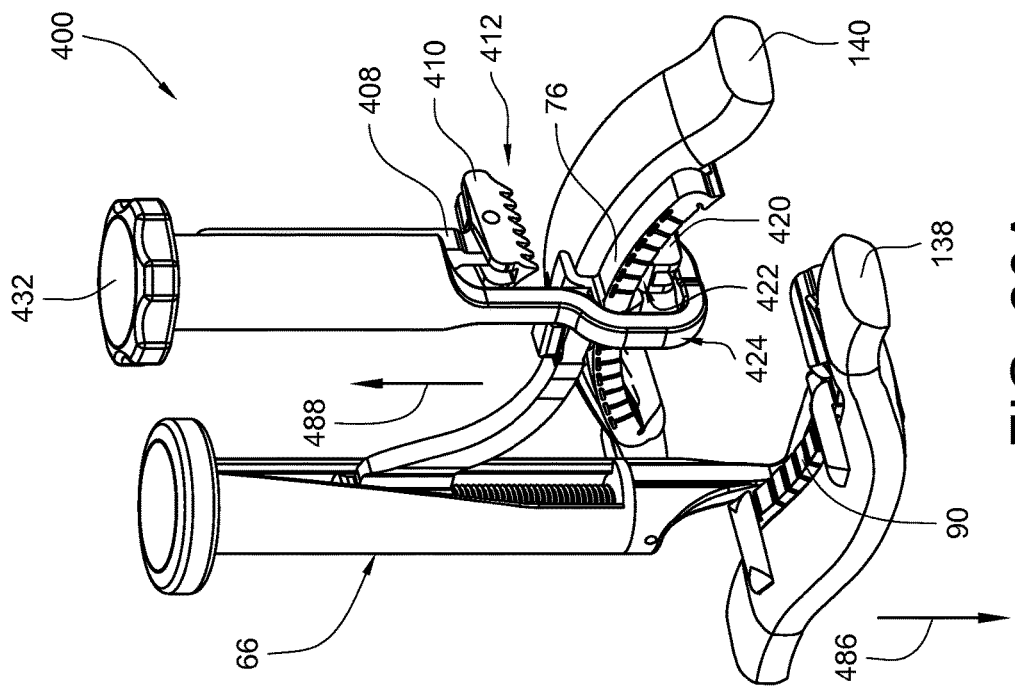

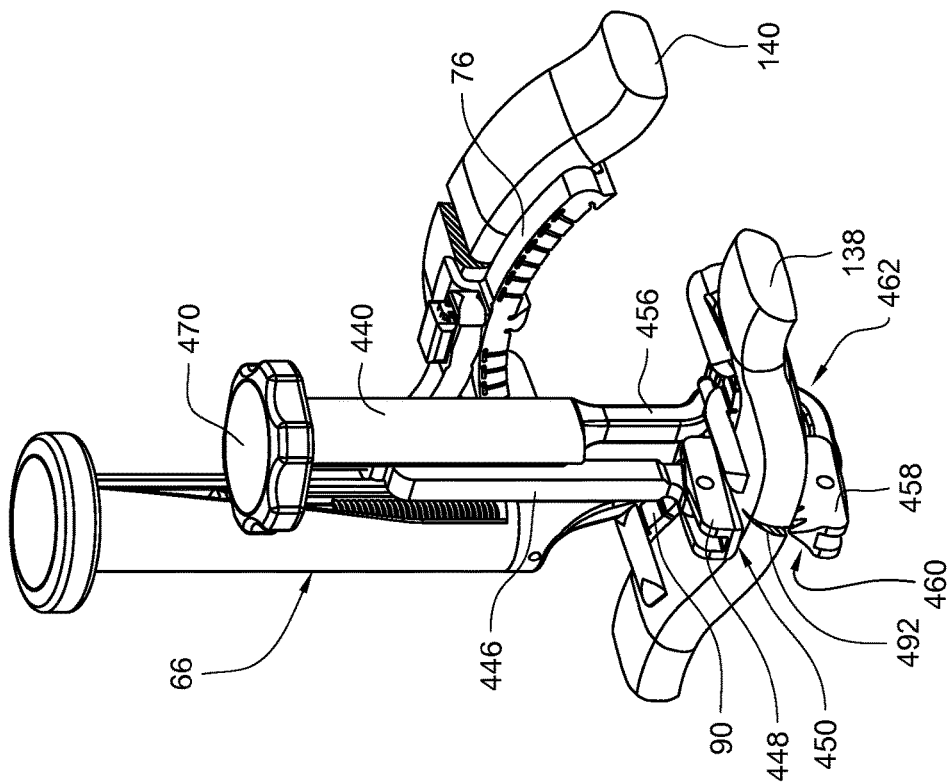
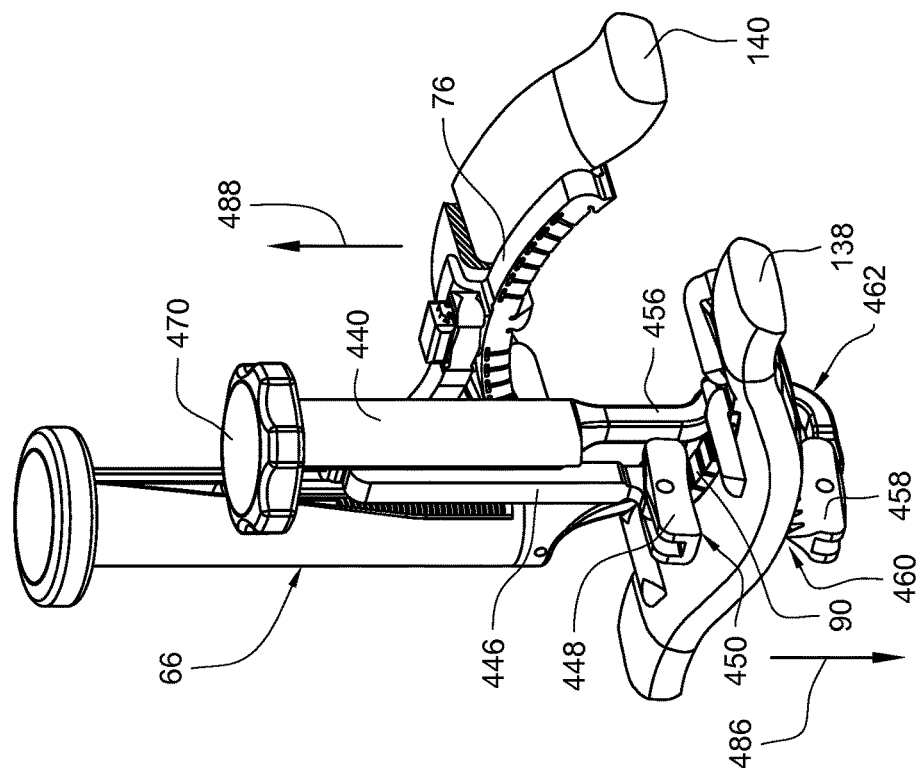

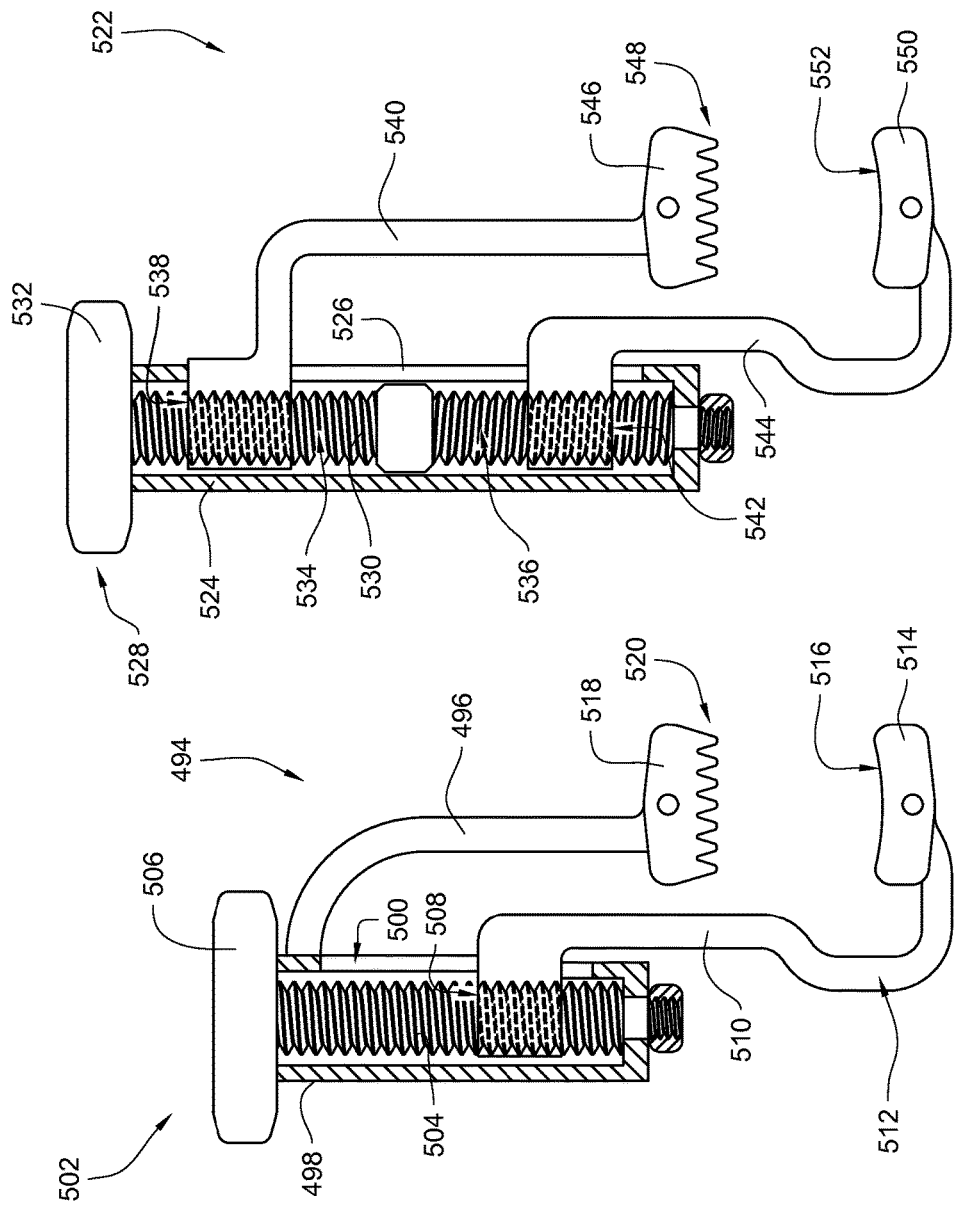

SURGICAL RIB CUTTER AND METHODS THEREOF

RELATED APPLICATION

This patent application claims priority to U.S. Provisional Patent Application No. 62/092,222 filed Dec. 15, 2014 and entitled "MINIMALLY INVASIVE SURGICAL TOOLS AND METHODS THEREOF". The entire 62/092,222 specification is hereby incorporated in its entirety.

FIELD

The claimed invention relates to rib cutting devices, and more specifically to surgical rib cutting devices for minimally invasive surgery.

BACKGROUND

Advances in cardiac surgery have enabled open heart and less-invasive methods for a wide variety of cardiac surgical procedures such as heart valve replacements or repairs. In many of these procedures, it is often necessary to retract tissue and bones in order to provide access to a surgical site. For example, in a sternotomy, where a vertical inline incision is made along the sternum, after which the sternum is divided or "cracked", a large sternum retractor, such as retractor 30 of FIG. 1A, is used to force the cracked sternum apart, providing access to the heart 32. This type of sternum retractor 30 has jaws 34, 36 which open in a single plane. While a sternotomy provides excellent access to the heart 32, the procedure is highly invasive and is associated with a high degree of post-operative pain and long recovery times for patients.

With advances in minimally invasive cardiac approaches, surgeons have been able move away from sternotomies for many procedures. For example, one favored approach to access the heart is to use a right anterior thoracotomy (a much smaller incision in the chest wall). The thoracotomy is often made between two adjacent ribs, and it is often necessary to spread those ribs apart to create an access window for the surgery. This can be done with a smaller version of the single plane style retractor shown in FIG. 1A, or, in some cases, with hand-manipulated retractors 38, 40 such as are shown in FIG. 1B. Hand manipulated retractors 38, 40 require an extra person's pair of hands, which may crowd the operating area around the patient. Hand retractors 38, 40 are also difficult to maintain in an open position over an extended period of time due. Therefore, a mechanical rib retractor may be favored over the hand-retractors, since it provides steady sustained retraction and may reduce operator fatigue and even the need for an additional person in the operating room.

Unfortunately, traditional thoracotomies, made through adjacent ribs, often do not provide enough access for certain types of cardiac procedures. While surgical instruments such as fiber optic scopes, forceps, cutting tools, and suturing tools may fit relatively well through a thoracotomy between adjacent ribs, replacement heart valves and their holders often do not (even when the adjacent ribs are spread apart with existing retractors). As a result, for many cardiac procedures, the thoracotomy often requires resection or removal of ribs in order to provide additional room for larger items, such as a replacement heart valve. While transection with or without reattachment of a rib can be less traumatic than a sternotomy, it would still be desirable to avoid excessive rib mobilization in order to provide less post-operative pain and quicker recovery times for patients.

Several other types of rib retractors have been developed in order to try to provide a larger access space between adjacent ribs. Before describing these retractors, however, it is helpful to consider different orientations of human anatomy so that the motion and operation of the refractors can be compared and contrasted according to how they move relative to the anatomy. Accordingly, human body 42 location references are illustrated in FIG. 2. Three anatomical planes are illustrated, dividing the body 42 into different sectors. The sagittal plane 44 divides into a left portion 46 and a right portion 48. The coronal plane 50 divides into an anterior (front) portion 52 and a posterior (back) portion 54. The transverse plane 56 divides into an upper portion 58 and a lower portion 60. A direction towards the head 62 may generally be referred to as a cephalad direction, while a direction towards the lower end of the spine 64 may generally be referred to as a caudad direction. Therefore, an axis running approximately in a direction from the head towards the lower portion of the body could be referred to as a substantially cephalad-caudal axis. Similarly, an axis running approximately in a direction from the back of the body to the front of the body could be referred to as a substantially anterior-posterior axis.

U.S. Pat. No. 5,865,731 discloses a surgical refractor that "is able to form an oblique tunnel-like opening at an incision site wherein, in addition to spreading the sides of the site incision substantially parallel to the contour of the patient's body, the ['731] surgical retractor additionally spreads the incision sides so that one side is depressed toward the patient and the other is directed outwardly from the patient." However, the rotational or offset positions for the grips must be predetermined before use since only one amount of anterior-posterior movement is possible during use. Furthermore, there is no spreading of the ribs in a cephalad-caudal direction without also having anterior-posterior separation. This may be undesirable since the additional anterior-posterior separation (and its resultant stress on the ribs) may not be needed for the entire duration of an operation.

U.S. Pat. No. 6,159,231 discloses a retractor having two racks movably attached at a nonlinear angle. When the first rack section is horizontally disposed, the other rack section is angled relative to the horizontal plane. The refractor may be ratcheted apart to spread adjacent ribs in a cephalad-caudal direction. One end of the retractor may also be lifted to spread the ribs in an anterior-posterior direction. The lifted end, however, must be held by hand or attached to a cable anchored to a support over the patient in order to maintain the anterior-posterior separation. This either requires additional personnel in the operating room, or modifications to the operating table/ceiling, neither of which is desirable as the additional equipment may get in the surgeon's way.

European Patent 792,620 discloses several embodiments of a rib retractor having adjustments to spread adjacent ribs in a cephalad-caudal direction. These retractors also have an adjustment to lift one rib relative to the other by contacting the patient somewhere else besides the ribs to create a fulcrum point for lifting leverage. Unfortunately, this additional contact point can cause additional bruising for the patient and may be difficult to use on obese patients.

European Patent 792,620 also discloses a version of a rib retractor where the spreader is attached to the operating table or to some platform which can be slid beneath the patient. This rib retractor has adjustments for both anterior-posterior separation as well as cephalad-caudal separation. While this embodiment alleviates the unnecessary bruising of previous models, its external anchoring system is also complex, cumbersome, and difficult to reposition.

European Patent 792,620 further discloses an embodiment of a rib retractor which spreads the ribs in a cephalad-caudal direction while simultaneously spreading the ribs in an anterior-posterior direction. However, like other examples from the prior art, there is no way to fine tune the opening, or to have one type of separation without the other, if desired, for a portion of the operation with this one retractor.

U.S. Pat. No. 6,416,468 discloses a rib retractor which can generate cephalad-caudal separation of the ribs, as well as an uneven amount of anterior-directed lift on the adjacent ribs. The '468 retractor has no opposing anterior-posterior rib movement. Furthermore, the '468 device employs a pivot point placed against the patient's body, somewhere in addition to the rib contact points, which can result in further bruising and discomfort.

Therefore, there is a need for a surgical rib retractor which can provide for varying and controlled amounts of rib separation in both a cephalad-caudal direction as well as an anterior-posterior direction without the need for external anchors or additional fulcrum points on the patient's body.

Surgical rib retractors may be used to displace or bend ribs in a variety of directions. Such displacement may cause certain ribs to fracture. Certain ribs are often surgically transected or even resected to provide for more rib displacement during retraction. Increased rib mobility enables further spreading of the adjacent soft tissue to provide greater access to the surgical site. If ribs unintentionally break during retraction, the fracture site may be suboptimal and have rough edges that may adversely affect healing. If one side (or plate) of a rib can remain intact while the other side is fractured, the intact area can act as a hinge while the opposing fracture site can provide for further bending of the rib during surgical retraction. The intact, hinged side of a rib can subsequently splint the opposing side of the fracture during healing. Bone fractures that occur on only one side of the bone, not through both sides, can occur from trauma (especially in the pediatric population with more supple bones) or are occasionally used in surgical procedures. This type of unilateral bony fracture is often referred to as a "green stick fracture" or a "green stick break." This references the type of break that can be induced in young, fresh or green tree limbs during controlled bending. When a green stick break occurs or is caused in a rib, it has a potential to be less traumatic for the patient as compared to a complete break since the rib still has some strength and support intact. The location of such a break may impact the degree of morbidity a patient experiences. For example, it would be undesirable for a green stick break to occur too close to the junction between the rib cartilage and the adjacent rib bone in the rib cage. Therefore, it would be advantageous to have a device that can induce a green stick break at a desired location to enable more controlled rib retraction. Rib retraction usually occurs in the same plane as the ribs. To enable more aggressive anterior to posterior rib displacement during their surgical retraction, it may be advantageous to induce an anterior green stick fracture on the anterior side being displaced in the anterior direction and a posterior green stick fracture in the posterior side of the rib being pushed in the posterior direction.

SUMMARY

A surgical rib cutter is disclosed. The surgical rib cutter includes a housing defining one or more guide slots. The surgical rib cutter also includes an anterior arm unit comprising an anterior effector configured to interact with an anterior side of a rib. The surgical rib cutter further includes a posterior arm unit comprising a posterior effector configured to interact with a posterior side of said rib. The surgical rib cutter also has an actuator movable relative to the housing and operationally coupled to at least one of the anterior and posterior arm units to move said at least one of the anterior and posterior arm units within at least one of the one or more guide slots to create a relative movement between the anterior and posterior arm units, said relative movement causing one of the anterior effector or the posterior effector to create a green stick break in said rib.

Another surgical rib cutter is disclosed. The surgical rib cutter includes a housing defining one or more guide slots. The surgical rib cutter also includes an anterior arm unit comprising an anterior effector having a cutting wedge and configured to interact with an anterior side of a rib. The surgical rib cutter further has a posterior arm unit. The posterior arm unit includes a posterior effector having a supporting pad and configured to interact with a posterior side of said rib. The posterior arm unit also includes a clearance bend configured to clear a rib retractor to allow the anterior and posterior effectors to interact with the anterior and posterior sides, respectively, of said rib while said rib is being retracted by the rib retractor. The surgical rib cutter also includes an actuator movable relative to the housing and operationally coupled to at least one of the anterior and posterior arm units to move said at least one of the anterior and posterior arm units within at least one of the one or more guide slots to create a relative movement between the anterior and posterior arm units, said relative movement causing the cutting wedge of the anterior effector to create a green stick break on the anterior side of said rib.

A further surgical rib cutter is disclosed. The surgical rib cutter includes a housing defining one or more guide slots. The surgical rib cutter also includes an anterior arm unit comprising an anterior effector having a supporting pad and configured to interact with an anterior side of a rib. The surgical rib cutter further has a posterior arm unit. The posterior arm unit includes a posterior effector having a cutting wedge and configured to interact with a posterior side of said rib. The posterior arm unit also has a clearance bend configured to clear a rib retractor to allow the anterior and posterior effectors to interact with the anterior and posterior sides, respectively, of said rib while said rib is being retracted by the rib retractor. The surgical rib retractor also includes an actuator movable relative to the housing and operationally coupled to at least one of the anterior and posterior arm units to move said at least one of the anterior and posterior arm units within at least one of the one or more guide slots to create a relative movement between the anterior and posterior arm units, said relative movement causing the cutting wedge of the posterior effector to create a green stick break on the posterior side of said rib.

BRIEF DESCRIPTION OF THE DRAWINGS

FIG. 1A schematically illustrates a prior art sternum retractor in use.

FIG. 1B schematically illustrates prior art handheld retractors in use during a thoracotomy.

FIGS. 6A and 6B show enlarged views of the anterior and posterior arm units of the surgical rib retractor of FIG. 3 in exploded and partially assembled views, respectively.

FIG. 11A schematically illustrates the surgical rib retractor of FIG. 9 being pivoted between two adjacent ribs.

FIG. 11B schematically illustrates the surgical rib retractor of FIG. 9 aligned with one rib and an adjacent rib.

FIG. 11C schematically illustrates the surgical rib refractor of FIG. 9 spreading adjacent ribs in both a posterior-anterior direction as well as in a cephalad-caudal direction.

FIG. 11D schematically illustrates the surgical rib refractor of FIG. 9 spreading the adjacent ribs of FIG. 11C further in both a posterior-anterior direction as well as in a cephalad caudal direction.

FIGS. 15-17 illustrate a further embodiment of a surgical rib retractor and its operation.

FIG. 20A schematically illustrates the rib cutter of FIG. 18A, aligned to be applied to a rib retracted in an anterior direction.

FIG. 20B schematically illustrates a resultant "green stick break" created on the anterior side of the rib retracted in the anterior direction from FIG. 20A, as caused by the rib cutter of FIG. 18A when applied to the rib.

FIG. 20C schematically illustrates the rib cutter of FIG. 18B, aligned to be applied to a rib retracted in a posterior direction.

FIG. 20D schematically illustrates a resultant "green stick break" created on the posterior side of the rib retracted in the posterior direction from FIG. 20C, as caused by the rib cutter of FIG. 18B when applied to the rib.

FIGS. 21 and 22 schematically illustrate further embodiments of a rib cutter, in an anterior configuration, for inducing a "green stick break" in a rib.

Figure 2:
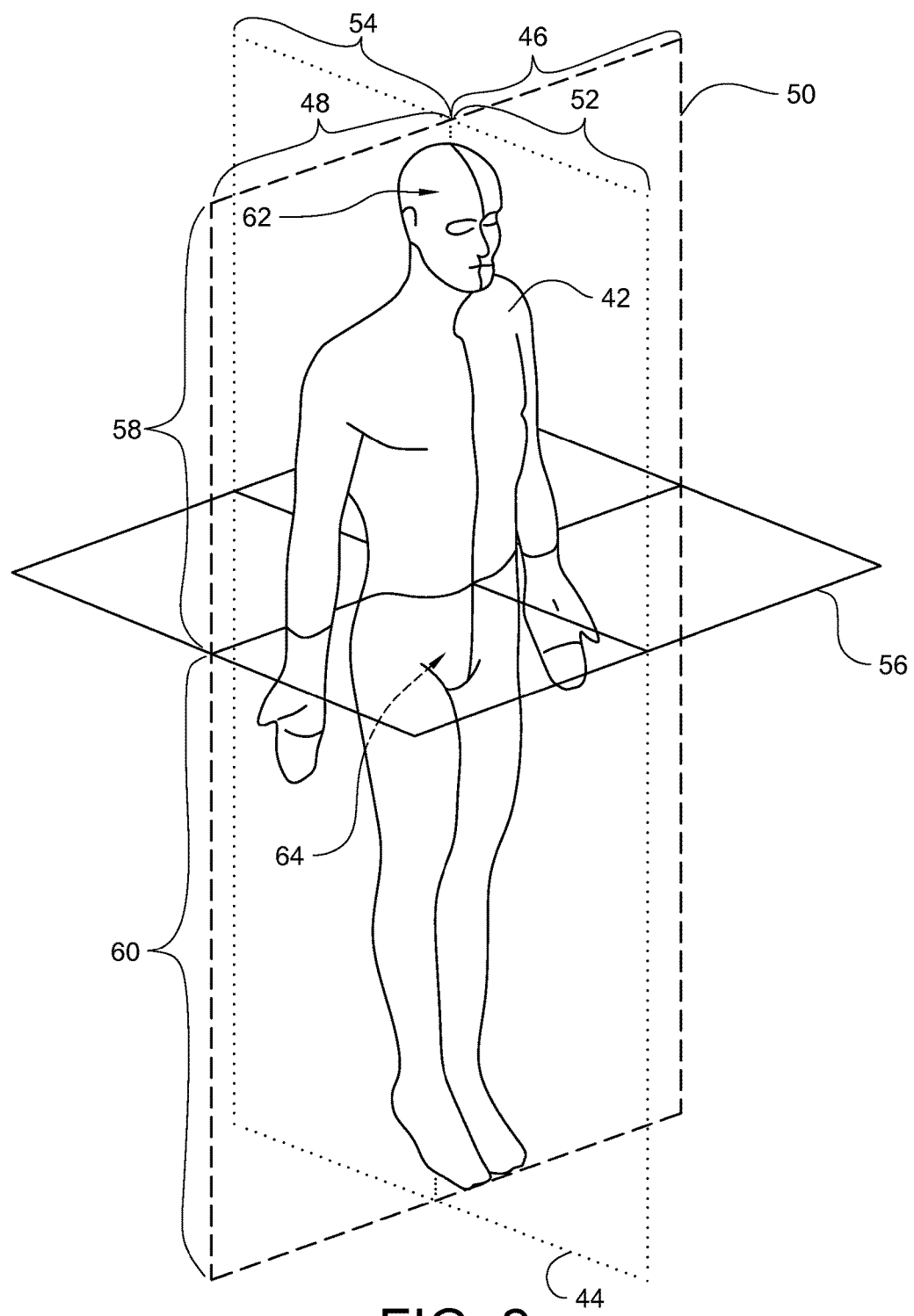
FIG. 2 illustrates several reference planes of a human body.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 3:
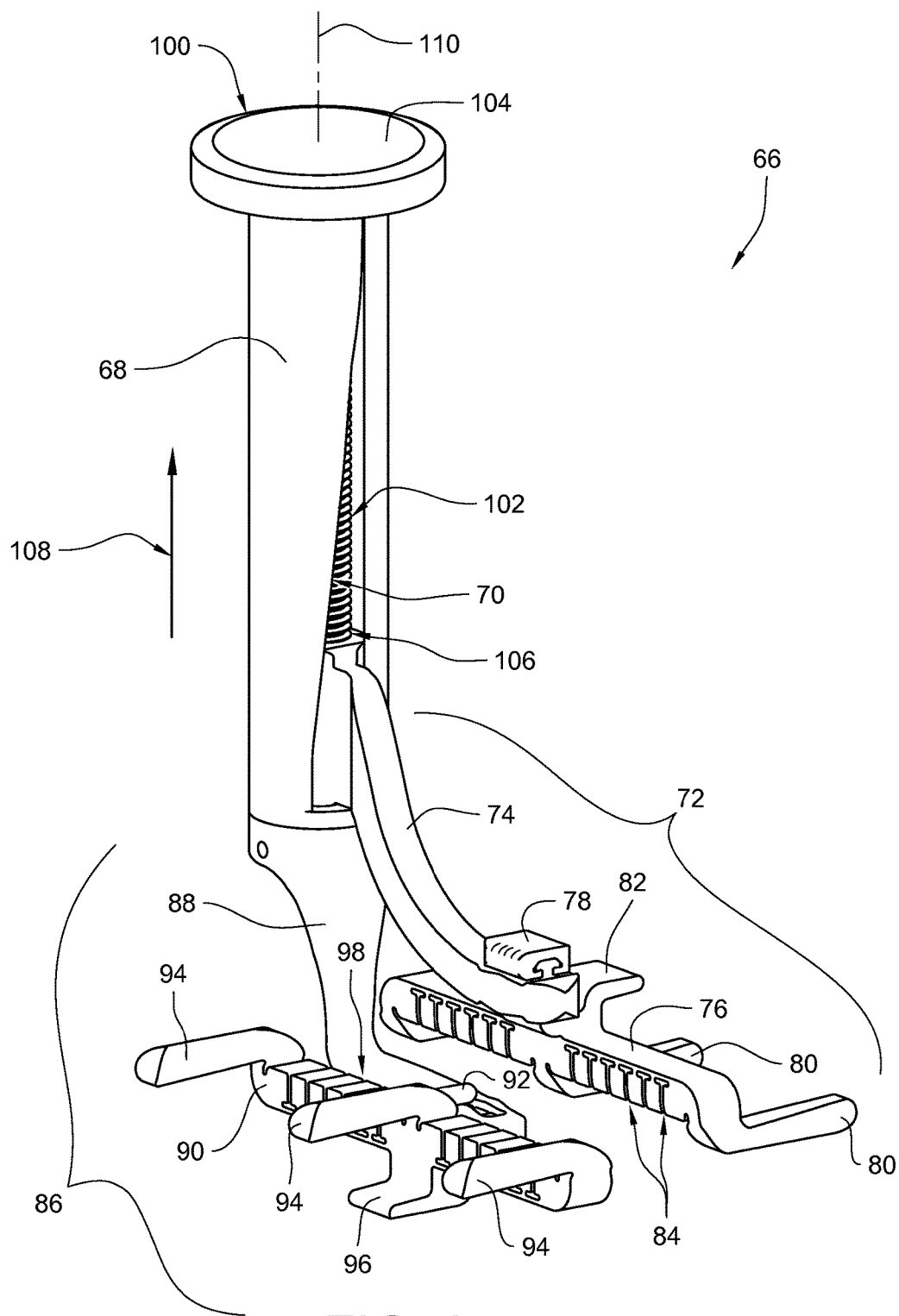
FIG. 3 is a perspective view of one embodiment of a surgical rib retractor.
Figure 4:
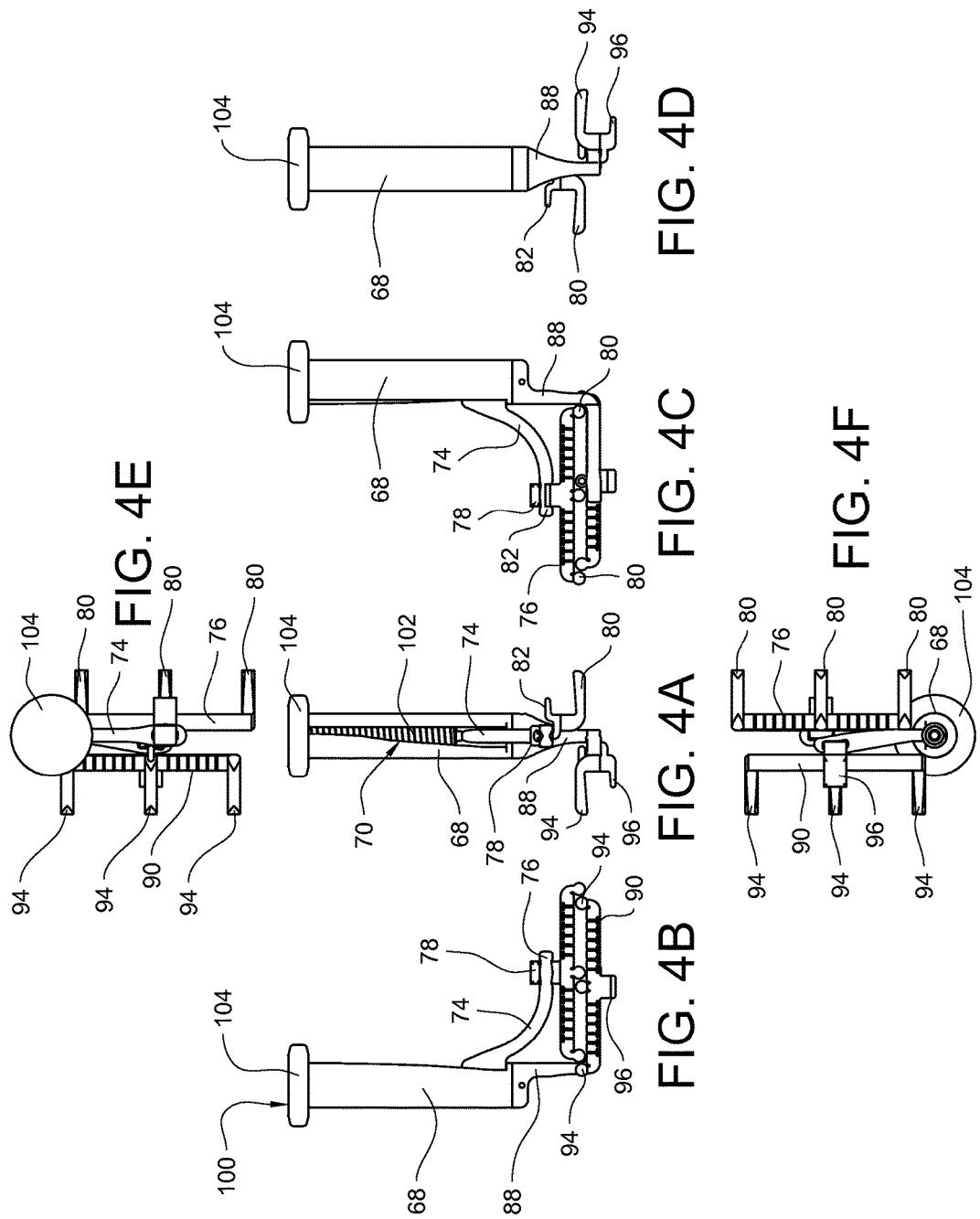
FIGS. 4A-4F are front, left, right, back, top, and bottom plan views, respectively, of the surgical rib retractor of FIG. 3.

FIG. 3 is a perspective view of one embodiment of a surgical rib retractor 66. The rib retractor 66 has a housing 68 having at least one cam surface 70. Depending on the embodiment, the housing may have a variety of shapes, including, but not limited to a substantially cylindrical shape (as illustrated in the embodiment of FIG. 3) or a substantially rectangular box shape. The cam surface 70 may have a substantially spiral profile, as illustrated in FIG. 3, that moves around at least a portion of the outside of the housing 68 as it stretches over at least a portion of the length of the housing 68. Depending on the embodiment, the cam surface 70 may have a substantially spiral profile or it may have a combination of at least one linear profile and at least one spiral profile.

The surgical rib retractor 66 also has an anterior arm unit 72 which is configured to receive one rib. The anterior arm unit 72 includes an anterior arm 74 and an anterior strut 76. In this embodiment, the anterior arm 74 and the anterior strut 76 are separate pieces held together by a keyed cap 78 which slides onto a corresponding portion of the anterior strut 76 which passes through the anterior arm 74. The anterior strut 76 has one or more rib engaging fingers 80 which work in conjunction with an opposing protuberance 82 in order to receive said one rib. In this embodiment, the opposing protuberance 82 is part of the strut 76, but in other embodiments, it may be part of the arm 74. Furthermore, in the embodiment of FIG. 3, the anterior arm 74 is not coupled to the housing 68.

The anterior strut 76 is preferably flexible in order to conform to a rib which it will bend in a generally anterior direction. Flexible embodiments of the anterior strut 76 may have this flexibility due to the elasticity of the material the strut 76 is made from. Other strut 76 embodiments may have flexibility due to the strut design itself. For example, some strut 76 embodiments may have one or more flexure voids 84 to increase the strut flexibility. Suitable strut 76 materials include, but are not limited to, metals, plastics, and other polymers.

The surgical rib retractor 66 also has a posterior arm unit 86 which is configured to receive an adjacent rib. The posterior arm unit 86 includes a posterior arm 88 and a posterior strut 90. In this embodiment, the posterior arm 88 and the posterior strut 90 are separate pieces held together by a pin 92 which slides into a corresponding portion of the posterior strut 90 while also engaging a portion of the posterior arm 88. The posterior strut 90 has one or more rib engaging fingers 94 which work in conjunction with an opposing protuberance 96 in order to receive the rib. In this embodiment, the opposing protuberance 96 is part of the strut 90, but in other embodiments, it may be part of the arm 88. Furthermore, in the embodiment of FIG. 3, the posterior arm 88 is coupled to the housing 68.

The posterior strut 90 is preferably flexible in order to conform to a rib which it will bend in a generally posterior direction. Flexible embodiments of the posterior strut may have this flexibility due to the elasticity of the material the strut 90 is made from. Other strut 90 embodiments may have flexibility due to the strut design itself. For example, some strut 90 embodiments may have one or more flexure voids 98 to increase the strut flexibility. Suitable strut 90 materials include, but are not limited to metals, plastics, and other polymers.

The surgical rib refractor 66 also has an actuator 100 movable relative to the housing 68 and operationally coupled, in this embodiment, to the anterior arm unit 72. In this embodiment, the actuator 100 includes a drive screw 102 and a knob 104 coupled to the drive screw 102 for turning the drive screw 102. The anterior arm 74 of the anterior arm unit 72 has a threaded portion 106 which corresponds to the threads on the drive screw 102. As the knob 104 is turned in a first direction, the drive screw 102 is rotated in the same first direction, and the threaded portion 106 of the anterior arm 74 will move up the drive screw 102 in a generally anterior direction 108. As the anterior arm 74 moves up the drive screw 102, the anterior arm 74 of the anterior arm unit 72 is moved by the actuator 100 against the cam surface 70, creating a relative movement between the anterior arm unit 72 and the posterior arm unit 86. This relative movement has at least two directional components. In this embodiment, the at least two directional components include a first direction which is substantially parallel to a longitudinal axis 110 of the drive screw 102. Since the cam surface 70 spirals around the housing 68 as it moves up the housing, the second directional component will be in a plane substantially perpendicular to the longitudinal axis 110 of the drive screw 102. Depending on the embodiment, and more generically, the at least two directional components could be generalized by saying that the first component is parallel to a first axis and the second component is in a plane substantially perpendicular to the first axis.

Since there are many possible geometric descriptions and/or anatomical reference perspectives, there are further ways the at least two directional components of the relative movement between the anterior arm unit 72 and the posterior arm unit 86 could be described. As some non-limiting and not necessarily mutually exclusive examples: In some embodiments, the at least two directional components may include a linear component (in this case parallel to the drive screw 102) and an arcuate component (in this case, as the anterior and posterior arm units 72, 86 are rotated apart by the engagement of the anterior arm 74 with the cam surface 70). In other embodiments, the at least two directional components may include a first direction substantially parallel to an anterior-posterior axis and a second direction substantially parallel to a cephalad-caudal axis. In further embodiments, the at least two directional components may include a paratransverse component (substantially parallel to the transverse plane) and a paracoronal component (substantially parallel to the coronal plane). In still other embodiments, the at least two directional components may include a first component substantially parallel to an anterior-posterior axis and a second, parcoronal component.

The threads of drive screw 102 may be chosen by those skilled in the art to resist movement of the anterior arm 74 down the drive screw when retracted ribs are pushing back on the refractor struts 76, 90. Furthermore, depending on the embodiment, the drive screw 102 may be a single tap thread or multi-tap thread to provide more travel per turn of the knob 104. The diameter and grip of the knob 104 may also be selected as is known by those skilled in the art to provide a desired mechanical advantage to the operator when turning the knob.

In the embodiment of FIG. 3, the anterior arm 74 is a mobile arm movably coupled to the actuator 100 (via the drive screw 102), while the posterior arm 88 is a fixed arm coupled to the housing. Other embodiments may have different configurations, as will be discussed in later examples.

FIGS. 4A-4F are front, left, right, back, top, and bottom plan views, respectively, of the surgical rib retractor of FIG. 3, the elements of which have been discussed above.

Figure 5:
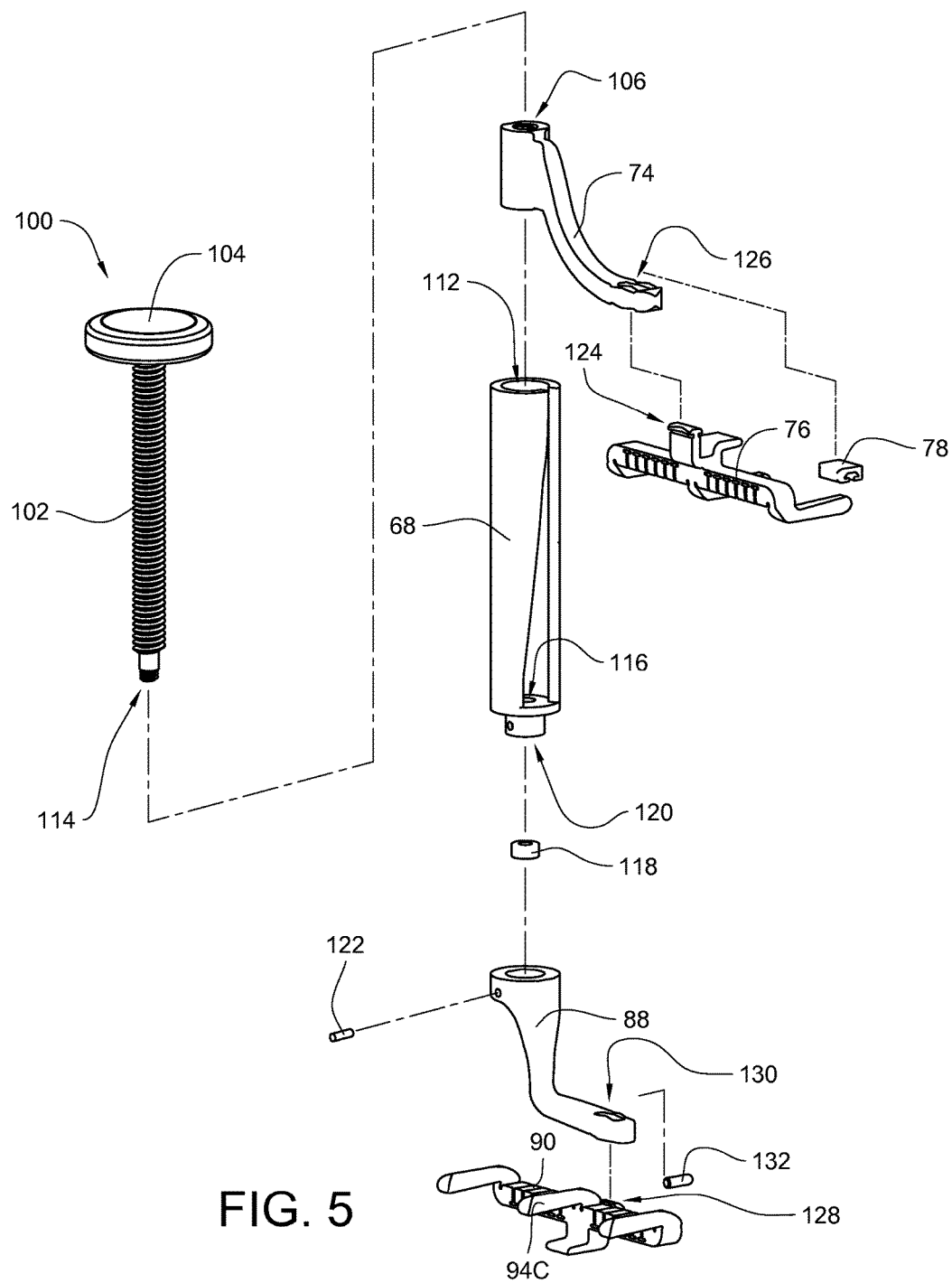
FIG. 5 is an exploded perspective view of the surgical rib retractor of FIG. 3.

FIG. 5 is an exploded perspective view of the surgical rib retractor of FIG. 3. As discussed previously, the actuator 100 has knob 104 and a drive screw 102. The drive screw 102 may be threaded into the corresponding threaded portion 106 of the anterior arm 74. This assembly can be dropped into an opening 112 in a first end of the housing 68. The end of the drive screw 114 opposite the knob 104 may be passed through a corresponding opening 116 in the second end of the housing 68. The end of the drive screw 114 may have a smaller diameter than the drive screw 102 so that it can act in conjunction with the corresponding opening 116 in the housing to help stabilize the drive screw in the housing 68. The end of the drive screw 114 may be threaded to engage a round nut 118 which sits inside a recess 120 in the bottom of the housing 68. The posterior arm 88 is fixedly coupled to the housing 68, for example, by a pin 122. Those skilled in the art will know a wide variety of alternate ways that the posterior arm 88 may be fixed to the housing 68, for example, by welding, gluing, or screwing.

A keyed portion 124 of the anterior strut 76 is passed up through an opening 126 in the anterior arm 74. The cap 78 slides onto the keyed portion 124 to keep the anterior strut 76 attached to the anterior arm 74. A wide variety of alternate ways for coupling the anterior strut 76 to the anterior arm 74 will be apparent to those skilled in the art and are intended to be included in the scope of the appended claims. Some embodiments may optionally have the anterior arm 74 and the anterior strut 76 be made as one continuous unit.

An alignment portion 128 of the posterior strut 90 is passed up through an opening 130 in the posterior arm 88. A pin 132 is pressed into a receiving hole (not visible in this view) located behind the central rib engaging finger 94C, above the posterior arm 88 where the alignment portion 128 engages the opening 130. The pin 132 prevents the posterior strut 90 from falling off of the posterior arm 88. A wide variety of alternate ways for coupling the posterior strut 90 to the posterior arm 88 will be apparent to those skilled in the art and are intended to be included in the scope of the appended claims. Some embodiments may optionally have the posterior arm 88 and the posterior strut 90 be made as one continuous unit.

FIGS. 6A and 6B show enlarged views of the anterior and posterior arm units of the surgical rib retractor of FIG. 3 in exploded and partially assembled views, respectively. In particular, FIGS. 6A and 6B show the shape of the alignment portion 128 of the posterior strut 90 with respect to its corresponding opening 130 in the posterior arm 88. Similarly, FIGS. 6A and 6B show the shape of the keyed portion 124 of the anterior strut 76 with respect to its corresponding opening 126 in the anterior arm 74. The openings 126, 130 have flared corners in this embodiment, thereby allowing the struts 76, 90 to pivot slightly with respect to their corresponding arms 74, 88 as schematically indicated by arrows 134, 136. This ability for the struts 76, 90 to pivot slightly with respect to their corresponding arms 74, 88 may help the struts in some embodiments to be fit between ribs, accounting for variations in anatomy from patient to patient. In other embodiments, however, the struts may not pivot relative to a corresponding arm.

In a real-life situation the rib retractors disclosed herein, and their equivalents, may be used to separate two ribs in more than one direction. The ribs would be accessed during a surgical procedure by making an incision between the desired ribs. FIGS. 7A-7D schematically illustrate how one embodiment of the rib retractor interacts with the ribs. For convenience only the ribs are shown with the retractor, but it should be understood that other tissues, blood vessels, and nerves would be involved in a real-life situation.

Figure 7B:
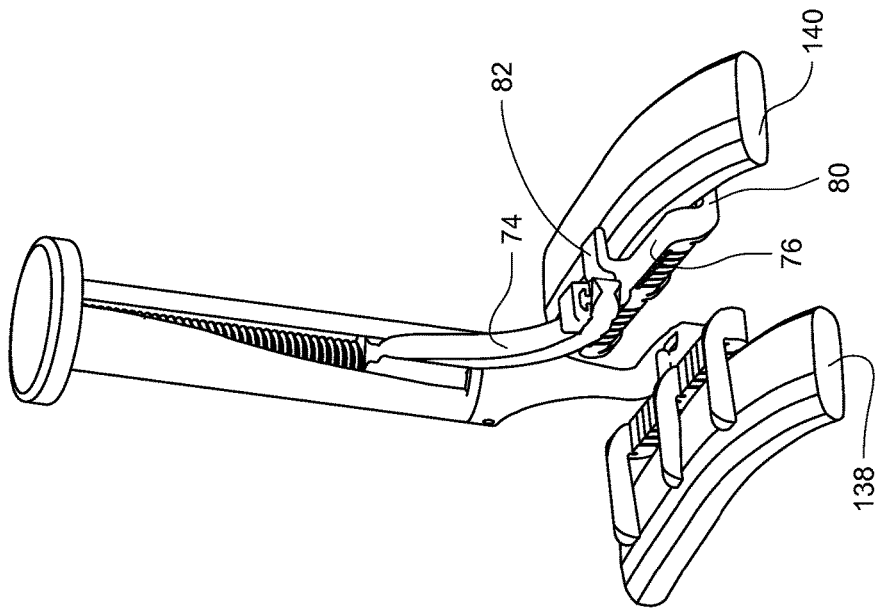
FIG. 7B schematically illustrates the surgical rib retractor of FIG. 3 engaging both anterior surface of one rib and the posterior surface of an adjacent rib.
Figure 7A:
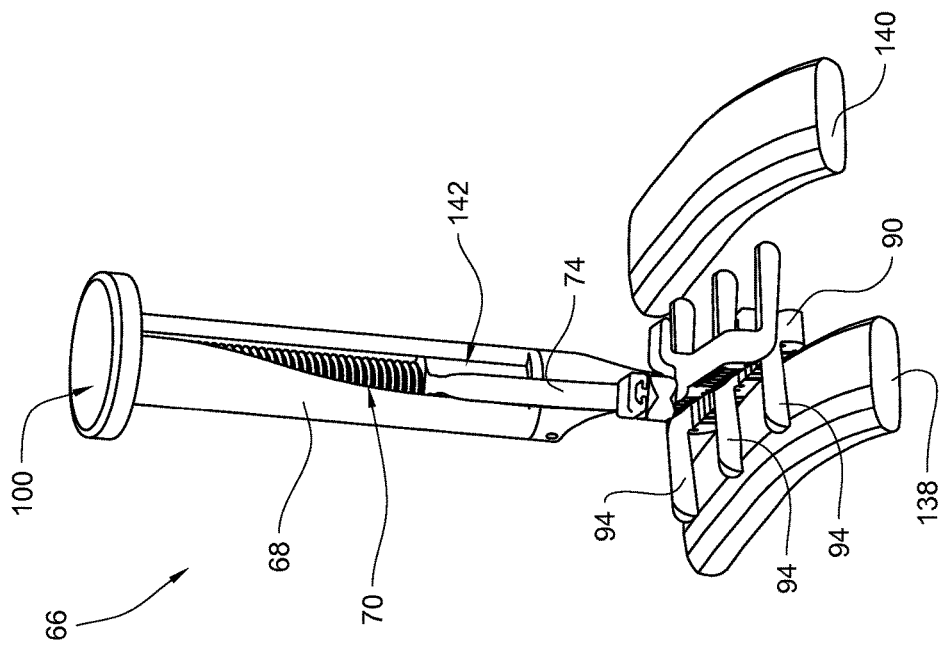
FIG. 7A schematically illustrates the surgical rib retractor of FIG. 3 engaging the anterior surface of a rib.

After an incision is made between the ribs 138, 140, the surgical rib retractor 66 may be inserted in the incision. As schematically illustrated in FIG. 7A, opposing protuberance 96 (not visible in this view) and the rib engaging fingers 94 of the posterior strut 90 are positioned around one rib 138. In this embodiment, the housing 68 has a wide opening 142 that allows the anterior arm 74 to swing back and forth while the arm 74 is lowered and not being driven against the cam surface 70 by the actuator 100. Accordingly, as illustrated in FIG. 7B, the anterior arm 74 may be swung towards the adjacent rib 140 so that the rib engaging fingers 80 and the opposing protuberance 82 of the anterior strut 76 are positioned around the adjacent rib 140.

Figure 7D:
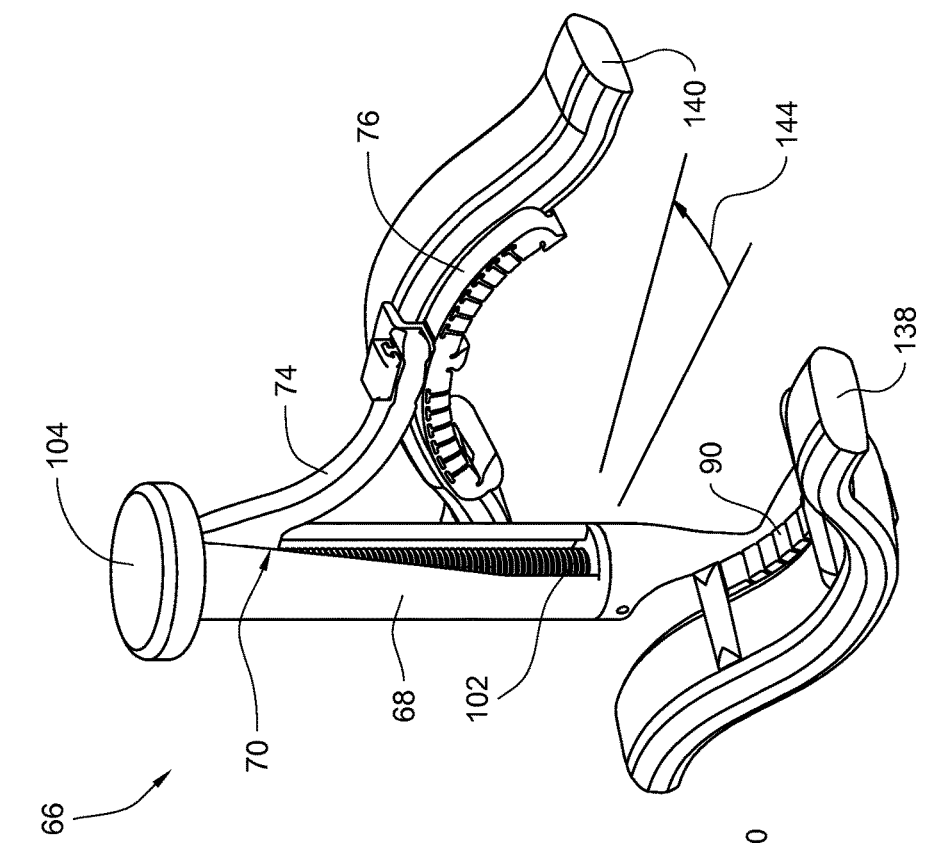
FIG. 7D schematically illustrates the surgical rib retractor of FIG. 3 spreading adjacent ribs in an anterior-posterior direction as well as in a cephalad-caudal direction.
Figure 7C:
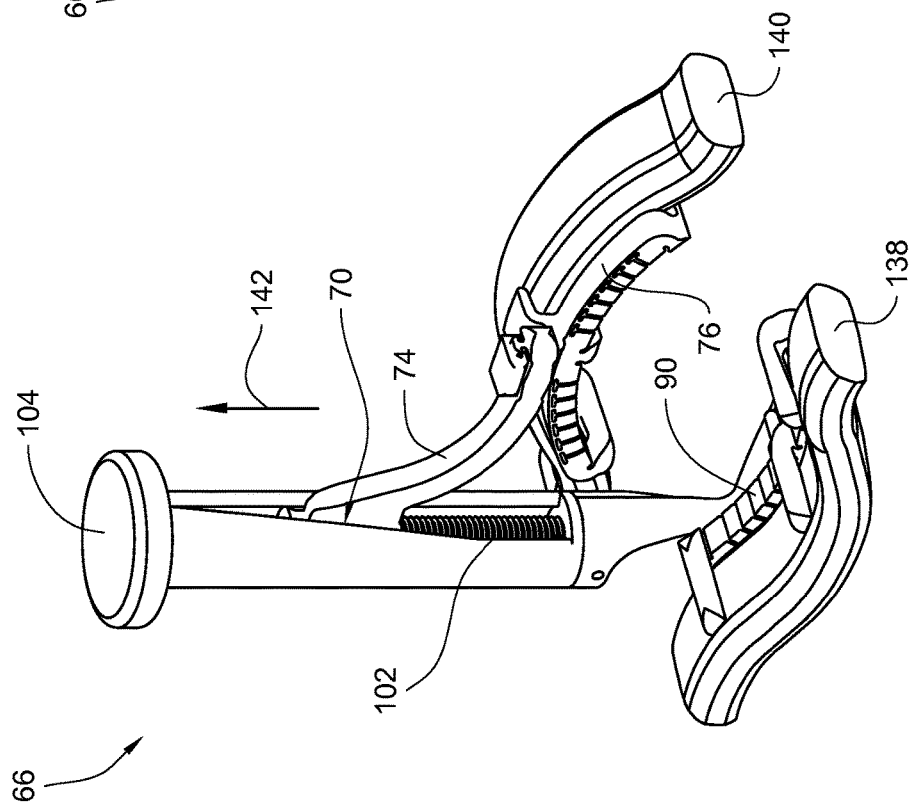
FIG. 7C schematically illustrates the surgical rib retractor of FIG. 3 spreading adjacent ribs in a posterior-anterior direction.

Now that the posterior and anterior struts 90, 76 have received their respective ribs 138, 140, the actuator knob 104 may be turned, causing drive screw 102 to move the anterior arm 74 up the drive screw 102 in a first direction 142, as illustrated in FIG. 7C. Depending on the embodiment, the anterior arm 74 will contact the cam surface 70 right away or in some cases after travelling up the drive screw 102 for a first distance. Since the rib retractor 66 is only contacting the patient's body where the two struts 76, 90 are receiving the ribs 138, 140, the travel of the anterior arm 74 up the drive screw 102 creates a relative movement between the posterior strut 90 and the anterior strut 76. Accordingly, as illustrated in FIG. 7C, the adjacent ribs 138,140 are being spread in a substantially anterior-posterior direction. One rib 138 is being bent in a generally posterior direction by the posterior strut 90, while another rib 140 is being bent in a generally anterior direction by the anterior strut 76.

In some situations, the opening created between the ribs 138, 140 at this point (FIG. 7C) may be large enough for some initial stages of a cardiac procedure, for example, while scopes are placed, access to a particular part of the heart is gained, and preparation of the surgical site is completed. However, in other situations, more access is needed, for example, when introducing a replacement heart valve into the thoracic cavity for further positioning into the heart. To increase the size of the access opening between the ribs 138, 140, the actuator knob 104 may be further turned, causing the anterior arm 74 to contact the cam surface 70 as the arm 74 moves farther up the drive screw 102, as illustrated in FIG. 7D. Since the cam surface 70 generally spirals around the outside of the housing 68, in addition to creating a relative movement between the anterior strut 76 and the posterior strut 90 parallel to a longitudinal axis of the drive screw 102, a relative angular separation 144 is created as well. The angular separation component can be specified as movement in a plane substantially perpendicular to the longitudinal axis of the drive screw 102 in this embodiment.

Figure 8:
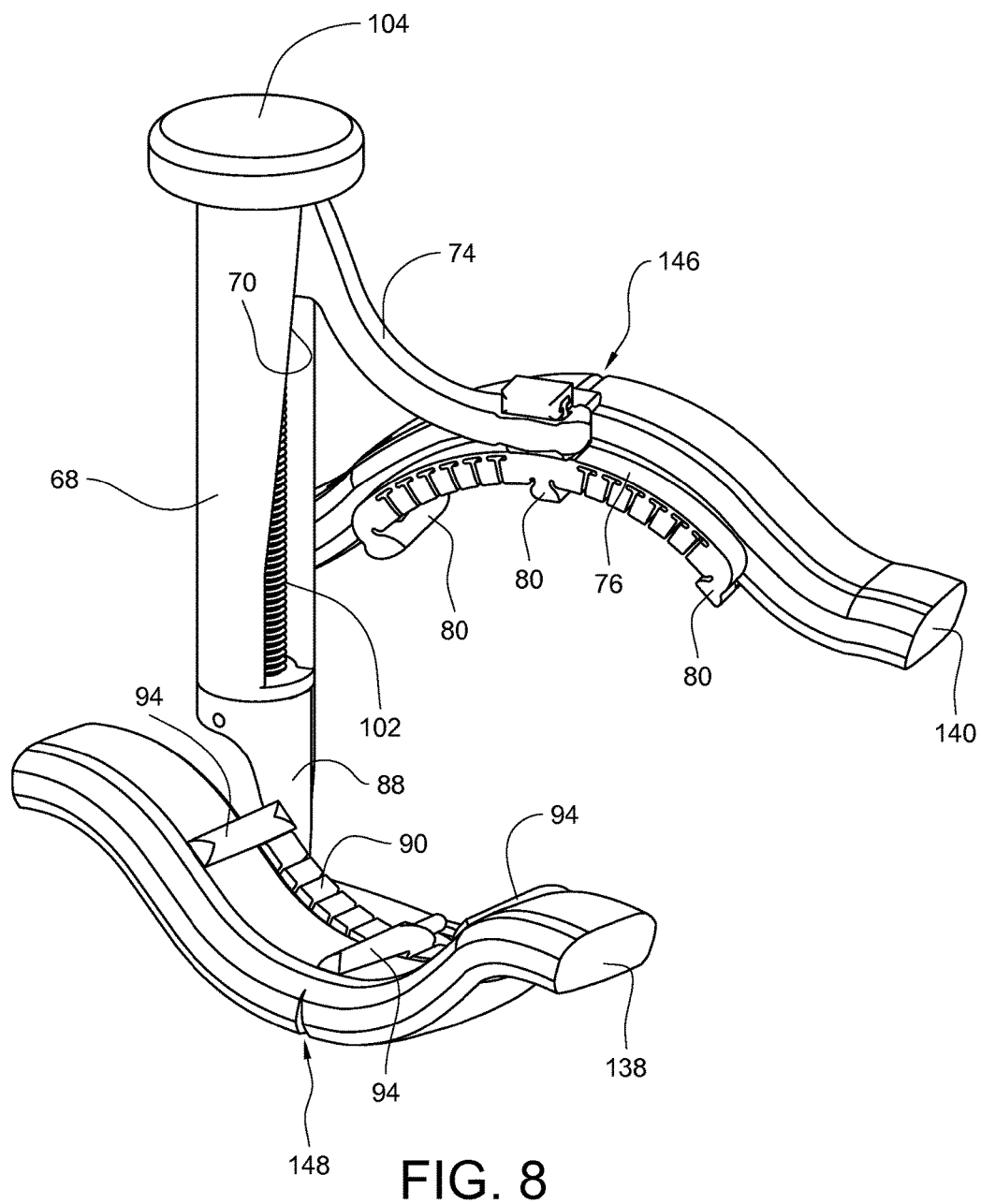
FIG. 8 schematically illustrates adjacent ribs being spread in an anterior-posterior direction as well as in a cephalad-caudal direction by the surgical rib retractor of FIG. 3, wherein each of the adjacent ribs has developed a "green stick break" on opposing sides of the respective ribs.

The farther the retractor 66 is opened, the more stress will be placed on the ribs 138, 140. By distributing the retraction forces between at least two directional components, it is possible in some cases that the ribs 138, 140 may not crack when under stress. In some situations, however, as schematically illustrated in FIG. 8, either or both of the posterior and anterior ribs 138, 140 may crack or break. Rib 140 is most likely to break 146 on the anterior side of the rib 140 since it is being bent in an anterior direction, but the break should not go all the way through the bone. This type of break is known as a "green stick break" as it mimics the behavior of a green tree branch that is bent until it breaks. Typically, such branches break on one side, while the other side of the branch, opposite the break, remains intact. Thus, the intact portion of the branch can act as a hinge. Conversely, rib 138 is most likely to break 148 on the posterior side of the rib 138 since it is being bent in a posterior direction, but the break should also be a green stick break. In cases where one or more green stick breaks 146, 148 occur, the opposite facing breaks 146, 148 will tend to self-splint each other on the adjacent ribs, which may help to improve patient healing times and reduce post-operative pain, especially as compared to other procedures which may be dissecting an entire rib to provide adequate thoracic access. Although breaks may be likely to occur near the mid-point of the bent rib as illustrated in FIG. 8, in some cases, the breaks may occur over a range of locations. In such cases, in order to avoid the uncertainty of a break location, a surgeon may wish to take measures to ensure the break occurs at a desired location.

Figure 9:
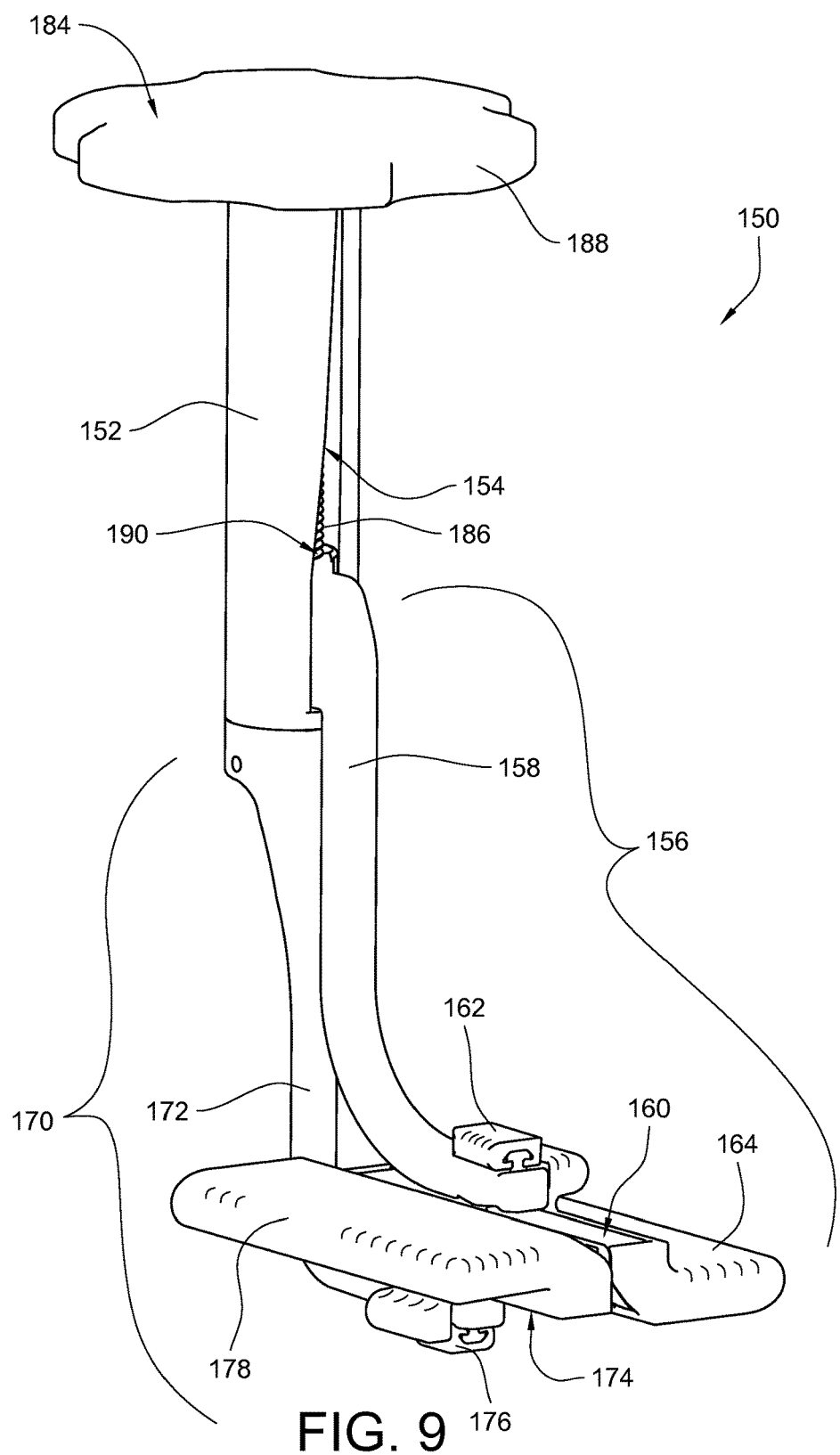
FIG. 9 is a perspective view of another embodiment of a surgical rib retractor.

FIG. 9 is a perspective view of another embodiment of a surgical rib retractor 150. The rib retractor 150 has a housing 152 having at least one cam surface 154. Depending on the embodiment, the housing 152 may have a variety of shapes, including, but not limited to a substantially cylindrical shape (as illustrated in the embodiment of FIG. 9) or a substantially rectangular box shape. The cam surface 154 may have a substantially spiral profile, as illustrated in FIG. 9, that moves around at least a portion of the outside of the housing 152 as it stretches over at least a portion of the length of the housing 152. Depending on the embodiment, the cam surface 154 may have a substantially spiral profile or may be a combination of a linear profile and a spiral profile.

Figure 10:
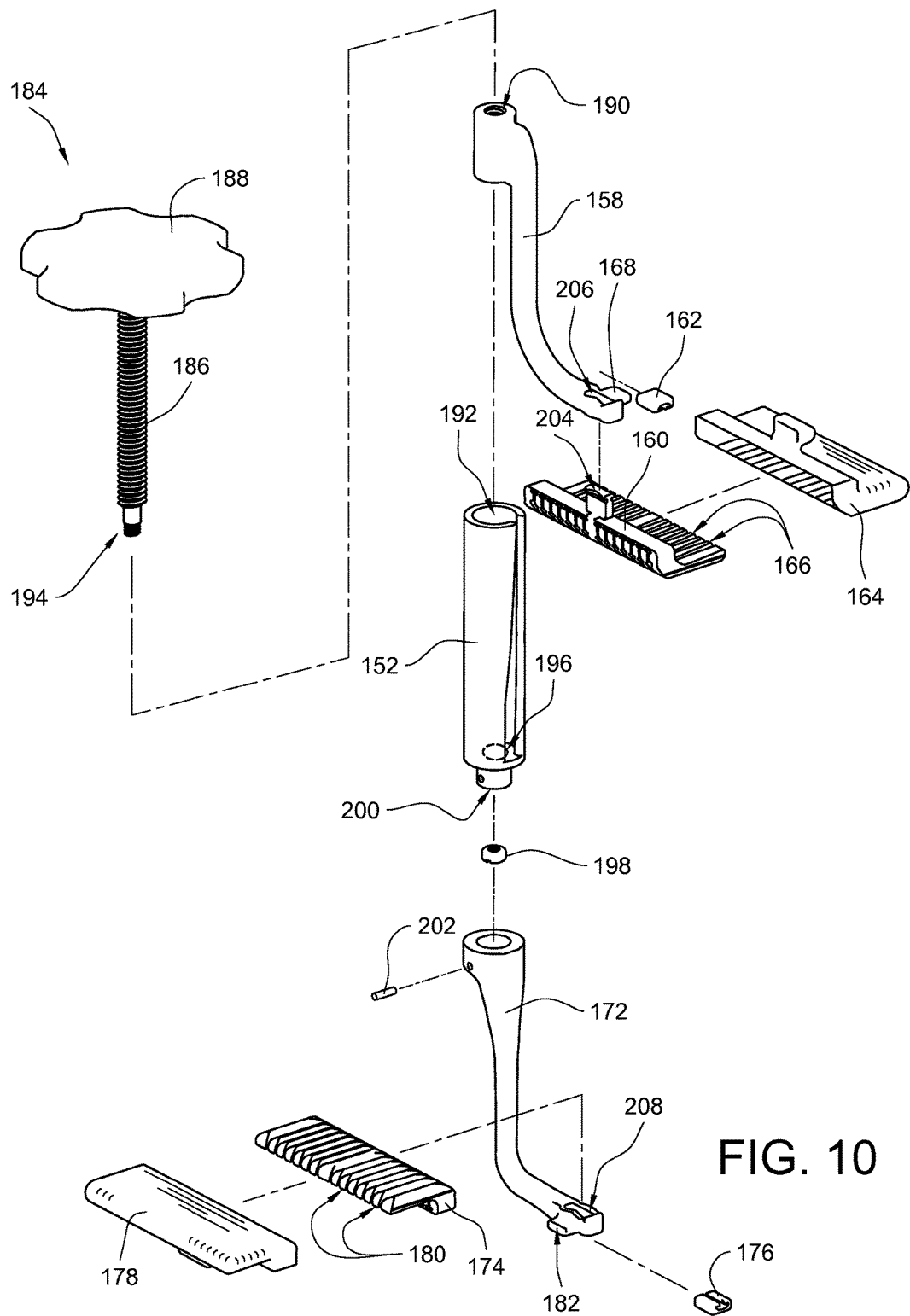
FIG. 10 is an exploded perspective view of the surgical rib retractor of FIG. 9.

The surgical rib retractor 150 also has an anterior arm unit 156 which is configured to receive one rib. The anterior arm unit 156 includes an anterior arm 158 and an anterior strut 160. In this embodiment, the anterior arm 158 and the anterior strut 160 are separate pieces held together by a keyed cap 162 which slides onto a corresponding portion of the anterior strut 160 which passes through the anterior arm 158. The anterior strut 160 has multiple rib engaging fingers which are not visible in this view because the rib engaging fingers are covered by an anterior shod 164. As with previous embodiments, the rib engaging fingers (covered by the shod 164) work in conjunction with an opposing protuberance (also covered by the shod 164) in order to receive said one rib. The anterior rib engaging fingers 166 and the opposing protuberance 168 may be seen in the exploded view of FIG. 10, as well as the sequence views of FIGS. 11A-11D, where the anterior shod 164 is not shown for clarity. In the embodiment of FIGS. 9-10, the opposing protuberance 168 is part of the anterior arm 158, but in other embodiments, it may be part of the strut 166. Furthermore, in the embodiment of FIG. 9, the anterior arm 158 is not coupled to the housing 152.

As with previous embodiments, the anterior strut 160 is preferably flexible in order to conform to a rib which it will bend in a generally anterior direction.

The surgical rib retractor 150 also has a posterior arm unit 170 which is configured to receive another rib. The posterior arm unit 170 includes a posterior arm 172 and a posterior strut 174. In this embodiment, the posterior arm 172 and the posterior strut 174 are separate pieces held together by a keyed cap 176 which slides into a corresponding portion of the posterior strut 174 which passes through the posterior arm 172. The posterior strut 174 has multiple rib engaging fingers which are not visible in this view because the rib engaging fingers are covered by a posterior shod 178. As with previous embodiments, the rib engaging fingers (covered by the shod 178) work in conjunction with an opposing protuberance (also covered by shod 178) in order to receive said another rib. The posterior rib engaging fingers 180 and the opposing protuberance 182 may be seen in the exploded view of FIG. 10, as well as the sequence views of FIGS. 11A-11D, where the posterior shod 178 is not shown for clarity. In the embodiments of FIGS. 9-10, the opposing protuberance is part of the posterior arm 172, but in other embodiments, it may be part of the strut 174. Furthermore, in the embodiment of FIG. 9, the posterior arm 172 is fixedly coupled to the housing 152.

As with previous embodiments, the posterior strut 174 is preferably flexible in order to conform to a rib which it will bend in a generally posterior direction.

The surgical rib retractor 150 also has an actuator 184 movable relative to the housing 152 and operationally coupled, in this embodiment, to the anterior arm unit 156. In this embodiment, the actuator 184 includes a drive screw 186 and a knob 188 coupled to the drive screw 186 for turning the drive screw 186. The anterior arm 158 of the anterior arm unit 156 has a threaded portion 190 which corresponds to the threads on the drive screw 186. As the knob 188 is turned in a first direction, the drive screw 186 is rotated in the same first direction, and the threaded portion 190 of the anterior arm 158 will move up the drive screw 186 and against the cam surface 154 in a manner similar to the previous embodiments already discussed.

The threads of drive screw 186 may be chosen by those skilled in the art to resist movement of the anterior arm 158 down the drive screw 186 when retracted ribs are pushing back on the retractor struts 160, 174. Furthermore, depending on the embodiment, the drive screw 186 may be a single tap thread or multi-tap thread to provide more travel per turn of the knob 188. The diameter and grip of the knob 188 may also be selected as is known by those skilled in the art to provide a desired mechanical advantage to the operator when turning the knob.

In the embodiment of FIG. 9, the anterior arm 158 is a mobile arm movably coupled to the actuator 184 (via the drive screw 186), while the posterior arm 172 is a fixed arm coupled to the housing 152. Other embodiments may have different configurations, as will be discussed in later examples.

FIG. 10 is an exploded perspective view of the surgical rib retractor of FIG. 9. As discussed previously, the actuator 184 has knob 188 and a drive screw 186. The drive screw 186 may be threaded into the corresponding threaded portion 190 of the anterior arm 158. This assembly can be dropped into an opening 192 in a first end of the housing 152. The end of the drive screw 194 opposite the knob 188 may be passed through a corresponding opening 196 in the second end of the housing 152. The end of the drive screw 194 may have a smaller diameter than the drive screw 186 so that it can act in conjunction with the corresponding opening 196 in a second end of the housing 152 to help stabilize the drive screw in the housing 152. The end of the drive screw 194 may be threaded to engage a round nut 198 which sits inside a recess 200 in the bottom of the housing 152. The posterior arm 172 is fixedly coupled to the housing 152, for example, by a pin 202. Those skilled in the art will know a wide variety of alternate ways that the posterior arm 172 may be fixed to the housing 152, for example, by welding, gluing, or screwing.

A keyed portion 204 of the anterior strut 160 is passed up through an opening 206 in the anterior arm 158. The cap 162 slides onto the keyed portion 204 to keep the anterior strut 160 attached to the anterior arm 158. A wide variety of alternate ways for coupling the anterior strut 160 to the anterior arm 158 will be apparent to those skilled in the art and are intended to be included in the scope of the appended claims. Some embodiments may optionally have the anterior arm 158 and the anterior strut 160 be made as one continuous unit.

Similarly, a keyed portion (not visible in FIG. 10 since it is pointing downward and hidden by the rib engaging fingers 180) of the posterior strut 174 is passed down through an opening 208 in the posterior arm 172. The cap 176 slides onto the posterior keyed portion (not visible) to keep the posterior strut 174 attached to the posterior arm 172. As before, a wide variety of alternate ways for coupling the posterior strut 174 to the posterior arm 172 will be apparent to those skilled in the art and are intended to be included in the scope of the appended claims. Some embodiments may optionally have the posterior arm 172 and the posterior strut 174 be made as one continuous unit.

As discussed above, an anterior shod 164 may be provided to slide over at least a portion of the rib engaging fingers 166 of the anterior strut 160. The shod 164 may also be configured to cover at least a portion of the opposing protuberance 168. Similarly, a posterior shod 178 may be provided to slide over at least a portion of the rib engaging fingers 180 of the posterior strut 174. The shod 178 may also be configured to cover at least a portion of the opposing protuberance 182.

In a real-life situation the rib retractors disclosed herein, and their equivalents, may be used to separate two ribs in more than one direction. The ribs would be accessed during a surgical procedure by making an incision between the desired ribs. FIGS. 11A-11D schematically illustrate how another embodiment of the rib retractor interacts with the ribs. This embodiment of a rib retractor is similar to the embodiment of FIGS. 9 and 10, however, for illustration purposes, the shods 164, 178 are not shown so that the rib engaging fingers may be seen more clearly. For convenience only the ribs are shown with the retractor, but it should be understood that other tissues, blood vessels, and nerves would be involved in a real-life situation.

After an incision is made between the ribs 138, 140, the surgical rib retractor 150 may be inserted in the incision. As schematically illustrated in FIG. 11A the housing 152 is tipped so that opposing protuberance 168 and the rib engaging fingers 166 of the anterior strut 160 may begin to be positioned around one rib 140. The housing 152 may be tilted back up, as illustrated in FIG. 11B, causing the anterior strut 160 to further engage the rib 140 while the opposing protuberance 182 and the rib engaging fingers 180 of the posterior strut 174 slide around the rib 138.

Now that the anterior and posterior struts 160, 174 have received their respective ribs 140, 138, the actuator knob 184 may be turned, causing drive screw 186 to move the anterior arm 158 up the drive screw 186 in a first direction 210 as illustrated in FIG. 11C. Depending on the embodiment, the anterior arm 158 will contact the cam surface 154 right away or in some cases after travelling up the drive screw 186 for a first distance. Since the rib retractor 150 is only contacting the patient's body where the two struts 160, 174 are receiving the ribs 140, 138, the travel of the anterior arm 158 up the drive screw 186 creates a relative movement between the posterior strut 174 and the anterior strut 160. Accordingly, as illustrated in FIG. 11C, the adjacent ribs 138, 140 are being spread in a generally anterior-posterior direction. The one rib 138 is being bent in a generally posterior direction by the posterior strut 174, while the other rib 140 is being bent in a generally anterior direction by the anterior strut 160.

In some situations, the opening created between the ribs 138, 140 at this point (FIG. 11C) may be large enough for some initial stages of a cardiac procedure, for example, while scopes are placed, access to a particular part of the heart is gained, and preparation of the surgical site is completed. However, in other situations, more access is needed, for example, when introducing a replacement heart valve into the thoracic cavity for further positioning into the heart. To increase the size of the access opening between the ribs 138, 140, the actuator knob 184 may be further turned, causing the anterior arm 158 to contact the cam surface 154 as the arm 158 moves farther up the drive screw 186, as illustrated in FIG. 11D. Since the cam surface 154 generally spirals around the outside of the housing 152, in addition to creating a relative movement between the anterior strut 160 and the posterior strut 174 parallel to a longitudinal axis of the drive screw 186, a relative angular separation 212 is created as well. The angular separation component can be specified as movement in a plane substantially perpendicular to the longitudinal axis of the drive screw 186 in this embodiment.

Figure 12:
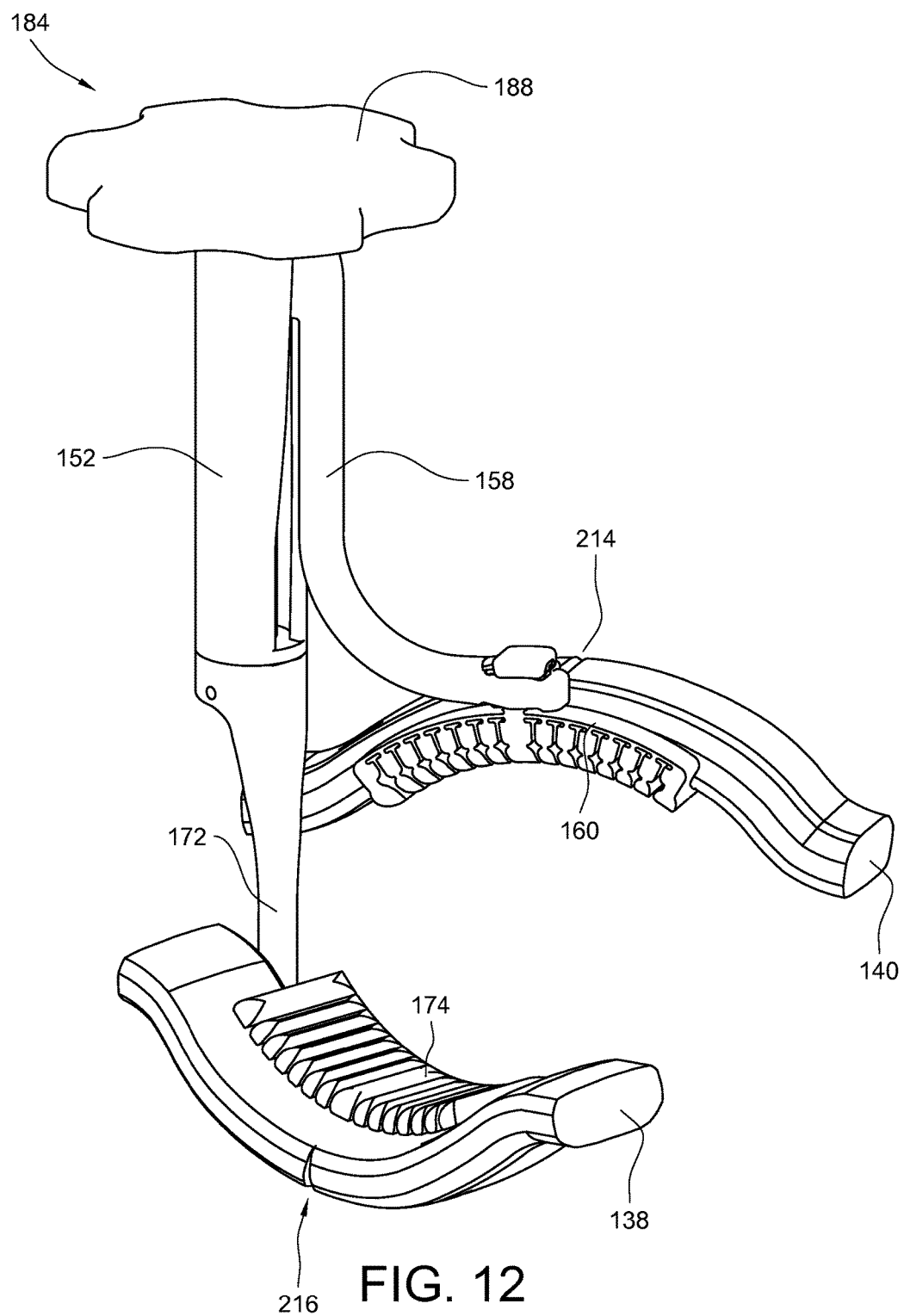
FIG. 12 schematically illustrates adjacent ribs being spread in an anterior-posterior direction as well as in a cephalad-caudal direction by the surgical rib retractor of FIG. 9, wherein each of the adjacent ribs has developed a "green stick break" on opposing sides of the respective ribs.

The farther the retractor 150 is opened, the more stress will be placed on the ribs 138, 140. By distributing the retraction forces between at least two directional components, it is possible in some cases that the ribs 138, 140 may not crack when under stress. In some situations, however, as schematically illustrated in FIG. 12, either or both of the posterior and anterior ribs 138, 140 may crack or break. In the case of the anterior rib 140, the rib is most likely to break 214 on the anterior side of the rib 140 being bent in the anterior direction, but the break should not go all the way through the bone. As discussed previously, this type of break is known as a "green stick break", as it mimics the behavior of a green tree branch that is bent until it breaks. Typically, such branches break on one side, while the other side of the branch, opposite the break remains intact. Thus, the intact portion of the branch can act as a hinge. In the case of the posterior rib 138, the rib is most likely to break 216 on the posterior side of the rib 138 being bent in the posterior direction, but the break should also be a green stick break. In cases where one or more green stick breaks 214, 216 occur, the opposite facing breaks 214, 216 will tend to self-splint each other on the adjacent ribs, which may help to improve patient healing times and reduce post-operative pain, especially as compared to other procedures which may be dissecting an entire rib to provide adequate thoracic access. Although breaks may be likely to occur near the mid-point of the bent rib as illustrated in FIG. 12, in some cases, the breaks may occur over a range of locations. In such cases, in order to avoid the uncertainty of a break location, a surgeon may wish to take measures to ensure the break occurs at a desired location.

Figures 13A, 13B:
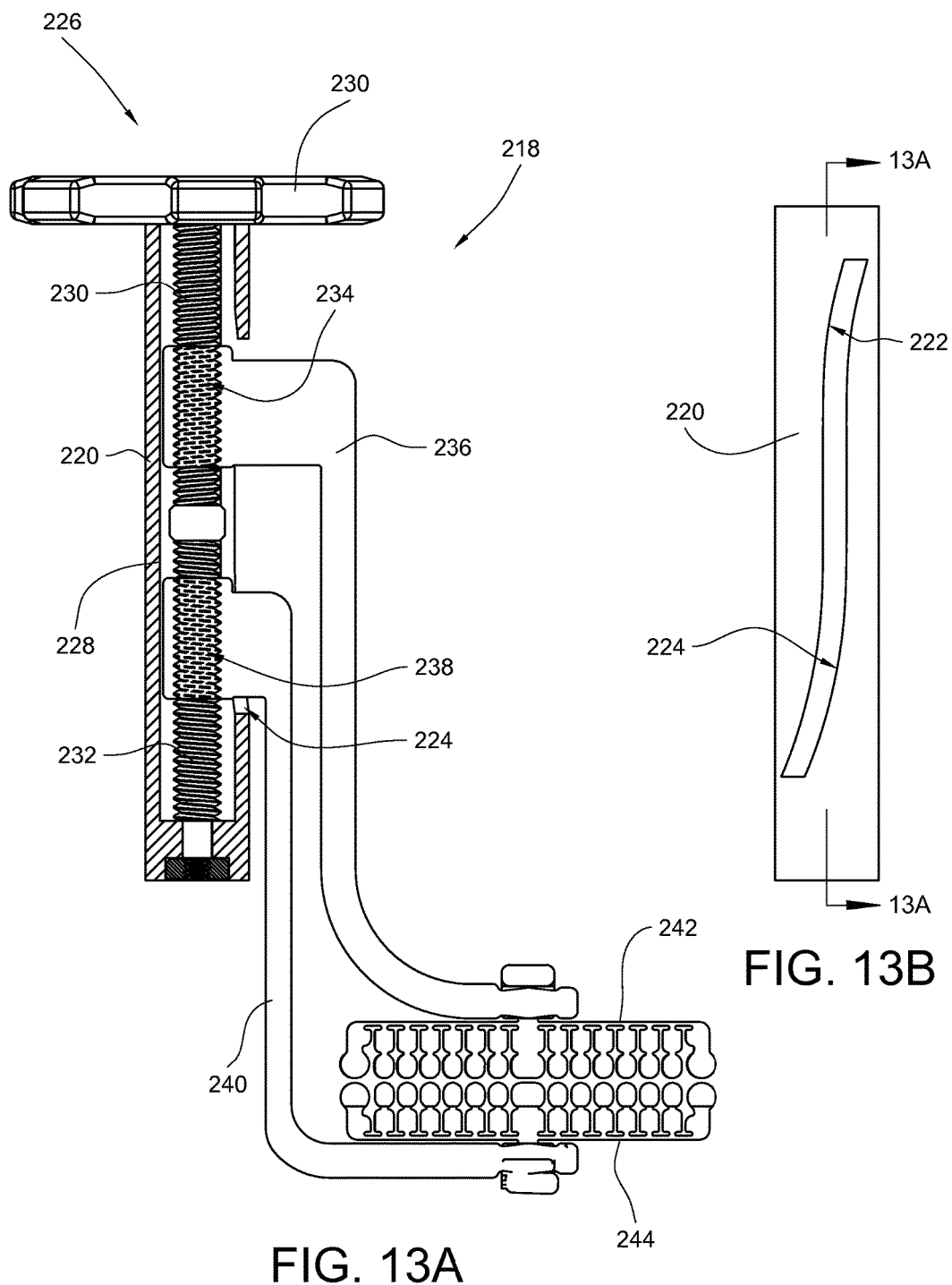
FIG. 13A illustrates a further embodiment of a surgical rib retractor in partial cross-sectional view.
FIG. 13B illustrates the housing of the surgical rib refractor of FIG. 13A in a non-cross-sectioned side view to highlight an embodiment of multiple cam surfaces.

FIG. 13A illustrates a further embodiment of a surgical rib retractor 218 in partial cross-sectional view front view. The retractor 218 has a housing 220 which has two cam surfaces: anterior cam surface 222 and posterior cam surface 224. FIG. 13B illustrates the housing 220 of the surgical rib retractor of FIG. 13A in a non-cross-sectioned right side view to help illustrate this embodiment of multiple cam surfaces 222, 224. As shown in FIG. 13A, the retractor 218 has an actuator 226 comprising a drive screw 228 and a knob 230 coupled to the drive screw 228 for turning the drive screw 228. In this embodiment, the drive screw 228 has an anterior threaded portion 230 and a posterior threaded portion 232. The threads of the anterior and posterior threaded portions 230, 232 are oriented in opposite directions.

In this embodiment, the anterior threaded portion 230 of the drive screw 228 is operationally coupled to a threaded portion 234 of an anterior arm 236. Similarly, the posterior threaded portion 232 of the drive screw 228 is operationally coupled to a threaded portion 238 of a posterior arm 240. The anterior arm 236 is coupled to an anterior strut 242, which together make an anterior arm unit which functions similarly to anterior arm units discussed above. The posterior arm 240 is coupled to a posterior strut 244, which together make a posterior arm unit which functions similarly to posterior arm units discussed above. When the knob 230 is turned, the anterior arm 236 is moved against the anterior cam surface 222, while the posterior arm 240 is moved oppositely against the posterior cam surface 224. This creates a relative movement between the anterior and posterior arm units. In the embodiment of FIG. 13A, neither the anterior arm 236 nor the posterior arm 240 are fixedly coupled to the housing 220.

Figure 14:
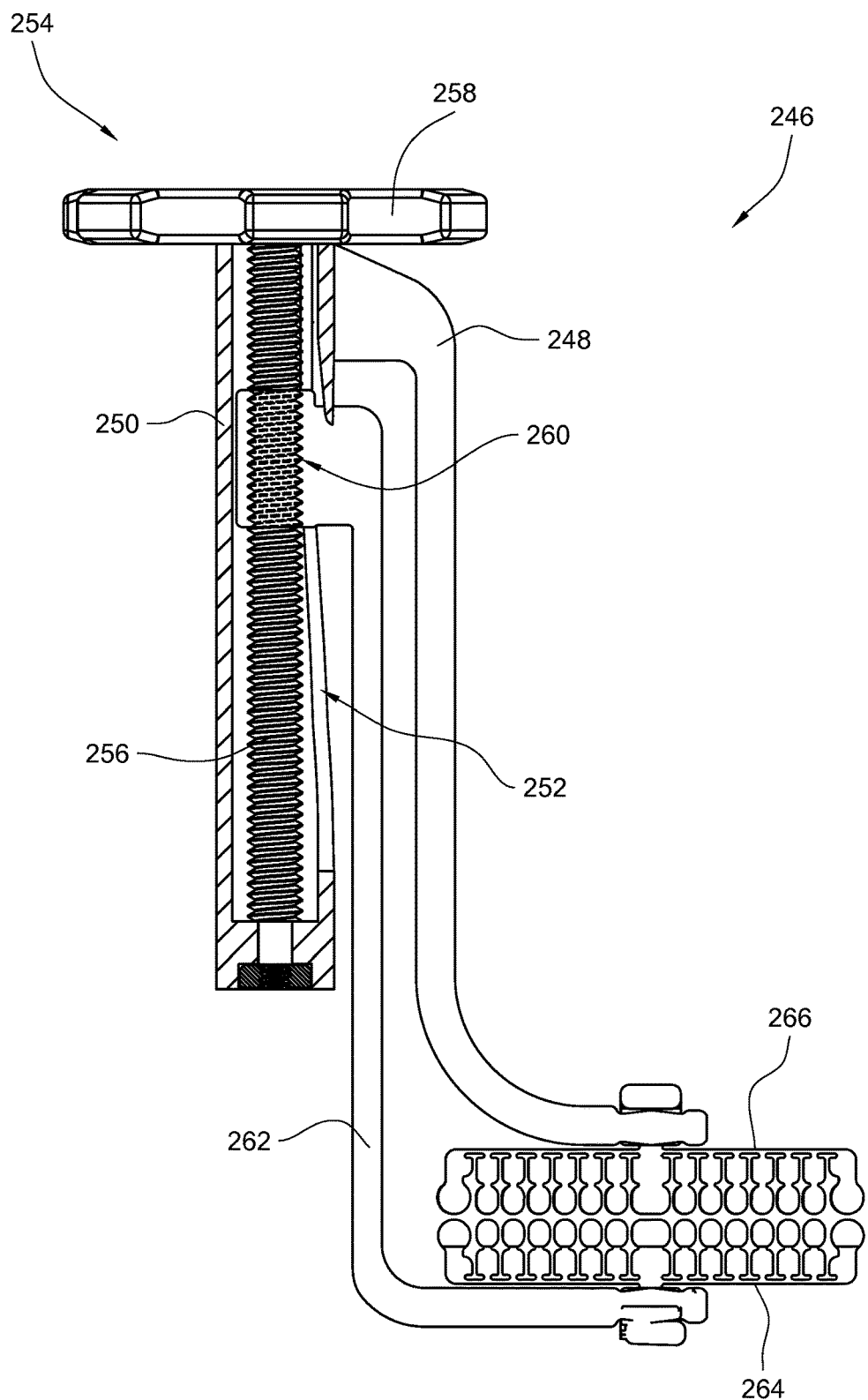
FIG. 14 illustrates another embodiment of a surgical rib retractor in partial cross-sectional view.

In many of the previous embodiments, the posterior arm of the rib retractor was fixedly coupled to the housing, while the anterior arm was movably coupled to a drive screw. FIG. 14, on the other hand, illustrates an embodiment of a surgical rib retractor 246, in partial cross-sectional view, where the anterior arm 248 is fixedly coupled to the housing 250. The housing 250 defines a cam surface 252. The retractor 246 has an actuator 254 comprising a drive screw 256 and a knob 258 coupled to the drive screw 256 for turning the drive screw 256. The drive screw 256 is operationally coupled to a threaded portion 260 of the posterior arm 262. The posterior arm 262 is coupled to a posterior strut 264, which together make a posterior arm unit which functions similarly to posterior arm units discussed above. The anterior arm 248 is coupled to an anterior strut 266, which together make an anterior arm unit which functions similarly to anterior arm units discussed above. When the knob 258 is turned, the posterior arm 262 is guided by the cam surface 252. Since the anterior arm 248 is fixed to the housing 250, this creates a relative movement between the anterior and posterior arm units.

In previous embodiments, the anterior and posterior arm units were configured to be moved relative to each other. As explained above, this relative movement comprises at least two directional components which may occur separately, concurrently, or in any combination thereof. One of the directional components may be in a direction substantially parallel to an anterior-posterior axis (or substantially parallel to a longitudinal axis of the retractor housing). Relative to this first directional component, however, in the previous embodiments, the anterior strut would only be able to deflect a rib it was coupled to in a generally anterior direction. Similarly, in the previous embodiments, relative to this first directional component, the posterior strut would only be able to deflect a rib it was coupled to in a generally posterior direction. In the arena of cardiac surgery, this would mean that, once the previous retractor embodiments were coupled to a pair of ribs, the retractor would tend to spread those ribs in such a way that 1) the heart's aortic root was visible/accessible or 2) the heart's aortic arch was visible/accessible, but not both, depending on which direction the retractor was facing when coupled to the ribs. Furthermore, with the previous embodiments, there is not a simple way to go back and forth between views of the aortic root and the aortic arch without removing the retractor, flipping it around, and then re-actuating the retractor.

FIG. 15 illustrates another embodiment of a surgical rib retractor 268. In this embodiment, however, the arm units of the retractor can be actuated to make either 1) the heart's aortic root or 2) the aortic arch visible without repositioning the device on the ribs. In FIG. 15, the rib retractor 268 is shown in a starting position. The retractor 268 has a housing 270 with first and second cam surfaces 272, 274. The retractor also has a first arm 276 and a second arm 278. A first strut 277 is coupled to the first arm. The first arm 276 and the first strut 277 make up a first arm unit. In some embodiments, the first arm and the first strut may be one continuous piece, as discussed previously. A second strut 279 is coupled to the second arm 278. The second arm 278 and the second strut 279 make up a second arm unit. The first strut 277 and the second strut 279 are similar to the struts discussed above, but they also have additional features in this embodiment. For example, both struts 277, 279 have flexure voids 277V and 279V, respectively, which encourage and/or enable the struts 277, 279 to be able to flex in either an anterior or a posterior direction. In this case, this is accomplished by the flexure voids 277V, 279V being present on both a posterior and an anterior side of their respective struts 277, 279. In other embodiments, the strut flexibility may be enabled or enhanced by material choice as discussed previously. Furthermore, in this embodiment, the first strut 277 has a plurality of opposing protrusions 277P opposite fingers 277F. Similarly, in this embodiment, the second strut 279 has a plurality of opposing protrusions 279P opposite fingers 279F. In this embodiment, the plurality of opposing protrusions 277P, 279P on each respective strut 277, 279 can operate as fingers, depending on how the device is used, as will be explained in more detail below.

The retractor 268 further has an actuator 280 which includes a knob 282 coupled to a drive screw 284. The second arm 278 is fixedly coupled to the housing 270. The first arm 276 has a threaded portion 286 which is operationally coupled to the drive screw 284. As the knob 282 is turned, the first arm 276 can be moved up or down the drive screw, depending on which direction the knob is turned. Thus, the actuator 280 is able to create relative movement between the first and second arm units.

In this embodiment, the threaded portion 286 of the first arm is located away from the ends of the drive screw 284 when the retractor is in a starting position, such as the one illustrated in FIG. 15. As illustrated in FIG. 16, if the knob 282 is rotated such that the turning drive screw 284 causes the threaded portion 286 of the first arm 276 to move up (generally anteriorly) towards the knob 282, then the first arm 276 will behave as an anterior arm (with fingers 277F pulling upward 288, generally anteriorly), while the relative movement compared to the second arm 278 will cause the second arm 278 to behave as a posterior arm (with the fingers 279F pushing downward 290, generally posteriorly). If the housing 270 is positioned on the sternum side of the ribs to which the struts 277, 279 may be coupled to, then the relative movement of the arms 276, 278 in this situation will tend to allow a surgeon to look 292 towards a patient's abdomen. In the case where the retractor is installed between the second and third ribs, this will tend to allow a surgeon to see/access the aortic root as schematically illustrated in FIG. 16 with a view of an aortic valve and the aortic root as might be exposed by an aortotomy.

As illustrated in FIG. 17, if the knob 282 is rotated such that the turning drive screw 284 causes the threaded portion 286 of the first arm 276 to move down (generally posteriorly) away from the knob 282, then the first arm 276 will behave as a posterior arm (with opposing protuberances 277P acting like fingers and pushing downward 294, generally posteriorly), while the relative movement compared to the second arm 278 will cause the second arm 278 to behave as an anterior arm (with opposing protuberances 279P acting like fingers and pulling upward 296, generally anteriorly). If the housing 270 is positioned on the sternum side of the ribs to which the struts 277, 279 may be coupled to, then the relative movement of the arms 276, 278 in this situation will tend to allow a surgeon to look 298 towards a patient's head. In the case where the refractor is installed between the second and third ribs, this will tend to allow a surgeon to see/access the aortic arch.

As described above, a surgical rib retractor may be used to displace or bend a rib in a variety of directions. Displacement in a generally anterior or generally posterior direction may cause certain ribs to fracture on the side of the rib under tension, resulting in a "green stick break" as discussed above. For simplicity, the example green stick breaks shown previously have been illustrated as occurring neatly and near the mid-point of the refractor portions which are engaging the rib. However, if a green stick break is going to form in this situation, it may not happen as cleanly or in a desired location on the rib. Therefore, as noted in the background of this specification, it would be advantageous to have a device which can influence the rib to form a green stick break at a desired location while the rib is in the process of being retracted.

Figures 18A, 18B:
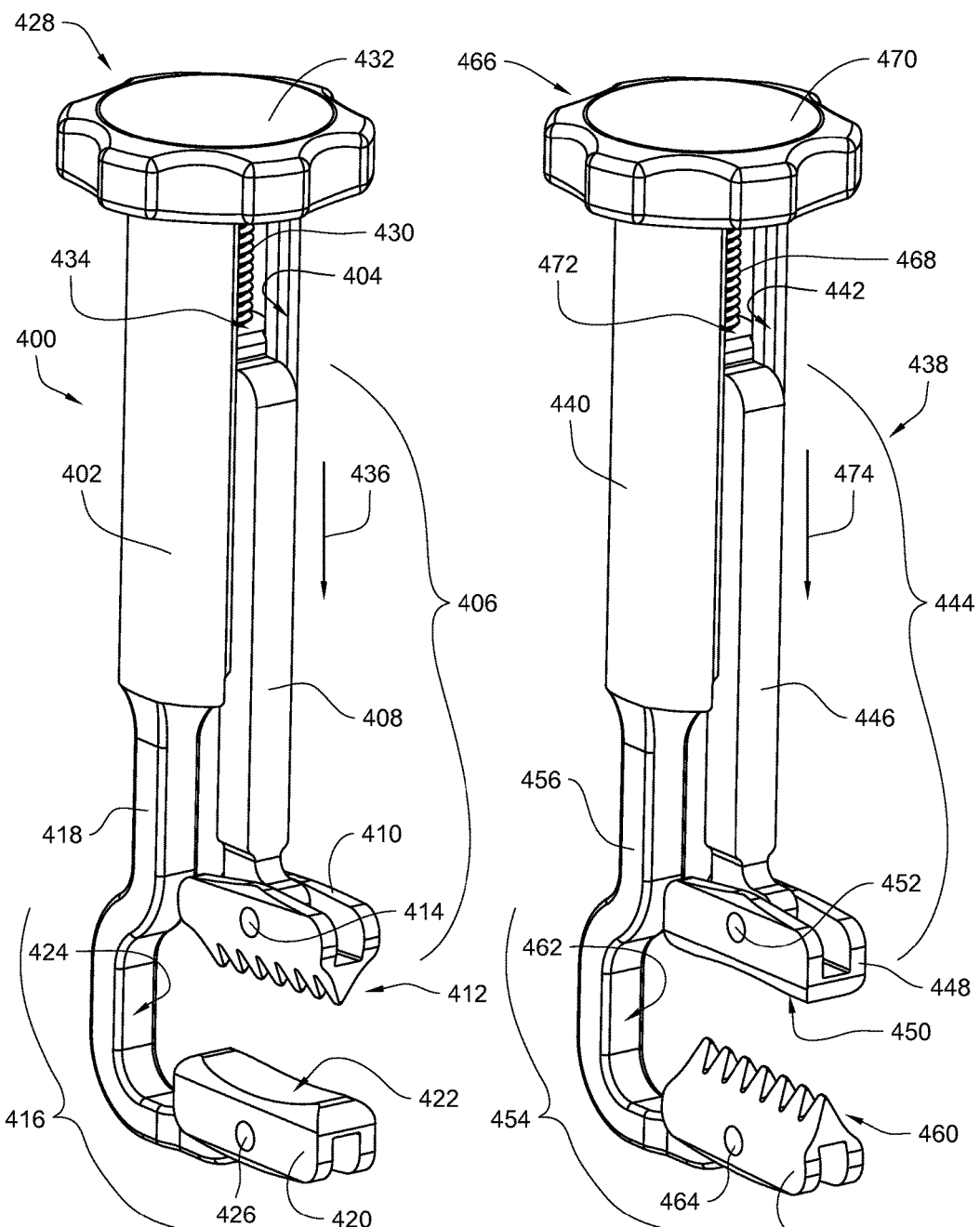
FIG. 18A is a perspective view of one embodiment of a rib cutter, in an anterior configuration, for inducing a "green stick break" in a rib.
FIG. 18B is a perspective view of another embodiment of a rib cutter, in a posterior configuration, for inducing a "green stick break" in a rib.

FIG. 18A is a perspective view of one embodiment of a surgical rib cutter 400. The rib cutter 400 has a housing 402 which defines a guide slot 404. Depending on the embodiment, the housing may have a variety of shapes, including, but not limited to a substantially cylindrical shape (as illustrated in the embodiment of FIG. 18A) or a substantially rectangular box shape. Although the guide slot 404 runs substantially straight and parallel to a longitudinal axis of the housing 402 in this embodiment, in other embodiments, the guide slot 404 may have a substantially spiral profile or cam-type surface profile, similar, but not limited to the types of cam surfaces discussed above with respect to the retractors.

The surgical rib cutter 400 also has an anterior arm unit 406 which is configured to engage an anterior side of a rib. The anterior arm unit 406 includes an anterior arm 408 and an anterior effector 410. In the embodiment of FIG. 18A, the anterior effector 410 comprises a cutting wedge 412. The cutting wedge may be made from a variety of materials, including, but not limited to metal, rubber, plastic, other polymers, or any combination and/or plurality thereof. The geometry of the illustrated cutting wedge is merely one example of a suitable wedge. Those skilled in the art will understand that a variety of wedge shapes may be used, including, but not limited to, those with pointed tips, rounded tips, blunted tips, chiseled tips, square tips, smooth edges, or serrated edges. The cutting wedge will have a shape which will encourage a rib under tension to form a green stick break in the vicinity of where the cutting wedge is pressed against the rib. Examples of this will be discussed in more detail below, with respect to FIGS. 20A-20D.

In the embodiment of FIG. 18A, the anterior arm 408 and the anterior effector 410 are separate pieces pivotably held together by a pivot pin 414. In other embodiments, the anterior arm 408 and the anterior effector 410 may be formed as a continuous piece. For embodiments where the anterior arm 408 and the anterior effector 410 are separate pieces, however, the anterior arm 408 and the anterior effector 410 do not necessarily have to have a pivoting connection.

The surgical rib retractor 400 also has a posterior arm unit 416 which is configured to engage a posterior side of the same rib. The posterior arm unit 416 includes a posterior arm 418 and a posterior effector 420. In the embodiment of FIG. 18A, the posterior effector 420 comprises a supporting pad 422. The supporting pad 422 may be made from a variety of materials, including, but not limited to metal, rubber, plastic, other polymers, or any combination and/or plurality thereof. The posterior arm 418 may have a clearance bend 424 in order to allow the cutter 400 to be positioned around one or more portions of a rib retractor, while that rib retractor is in use. To that end, the description of the posterior effector 420 as being configured to engage a posterior side of the rib should be interpreted as including, but not necessarily limited to, situations where the posterior effector 420 is in direct or indirect contact with the posterior side of the rib. In some situations, the posterior effector 420 may contact a portion of a rib retractor which is engaging the rib. Similarly, the description of the anterior effector 410 as being configured to engage an anterior side of the rib should be interpreted as including, but not necessarily limited to, situations where the anterior effector 410 is in direct or indirect contact with the anterior side of the rib.

In the embodiment of FIG. 18A, the posterior arm 418 and the posterior effector 420 are separate pieces pivotably held together by a pivot pin 426. In other embodiments, the posterior arm 418 and the posterior effector 420 may be formed as a continuous piece. For embodiments where the posterior arm 418 and the posterior effector 420 are separate pieces, however, the posterior arm 418 and the posterior effector 420 do not necessarily have to have a pivoting connection.

The surgical rib cutter 400 also has an actuator 428 movable relative to the housing 402 and operationally coupled, in this embodiment, to the anterior arm unit 406. In this embodiment, the actuator 428 includes a drive screw 430 and a knob 432 coupled to the drive screw 430 for turning the drive screw 430. The anterior arm 408 of the anterior arm unit 406 has a threaded portion 434 which corresponds to the threads on the drive screw 430. As the knob 432 is turned in a first direction, the drive screw 430 is rotated in the same first direction, and the threaded portion 434 of the anterior arm 408 will move down the drive screw 430 in a generally posterior direction 436. FIGS. 20A-20B will later illustrate how this can be useful when paired with a rib retractor.

In the embodiment of FIG. 18A, the anterior arm 408 is a mobile arm movably coupled to the actuator 428 (via the drive screw 430), while the posterior arm 418 is a fixed arm coupled to the housing 402. Other embodiments may have different configurations, as will be discussed in later examples.

The threads of drive screw 430 may be chosen by those skilled in the art to resist movement of the anterior arm 408 up the drive screw 430 when a rib is being compressed between the anterior and posterior effectors. Furthermore, depending on the embodiment, the drive screw 430 may be a single tap thread or multi-tap thread to provide more travel per turn of the knob 432. The diameter and grip of the knob 432 may also be selected as is known by those skilled in the art to provide a desired mechanical advantage to the operator when turning the knob 432.

In the embodiment of FIG. 18A, the anterior effector 410 comprises a cutting wedge 412, while the posterior effector 420 comprises a supporting pad 422. Such a configuration may be used to create a green stick break on an anterior side of a rib. The embodiment of FIG. 18B, however, can be used to create a green stick break on a posterior side of a rib.

FIG. 18B is a perspective view of another embodiment of a surgical rib cutter 438. The rib cutter 438 has a housing 440 which defines a guide slot 442. Depending on the embodiment, the housing 440 may have a variety of shapes, including, but not limited to a substantially cylindrical shape (as illustrated in the embodiment of FIG. 18B) or a substantially rectangular box shape. Although the guide slot 442 runs substantially straight and parallel to a longitudinal axis of the housing 440 in this embodiment, in other embodiments, the guide slot 442 may have a substantially spiral profile or cam-type surface profile, similar, but not limited to the types of cam surfaces discussed above with respect to the retractors.

The surgical rib cutter 438 also has an anterior arm unit 444 which is configured to engage an anterior side of a rib. The anterior arm unit 444 includes an anterior arm 446 and an anterior effector 448. In the embodiment of FIG. 18B, the anterior effector 448 comprises a supporting pad 450. The supporting pad 450 may be made from a variety of materials, including, but not limited to metal, rubber, plastic, other polymers, or any combination and/or plurality thereof. In this embodiment, the anterior arm 446 and the anterior effector 448 are separate pieces pivotably held together by a pivot pin 452. In other embodiments, the anterior arm 446 and the anterior effector 448 may be formed as continuous piece. For embodiments where the anterior arm 446 and the anterior effector 448 are separate pieces, however, the anterior arm 446 and the anterior effector 448 do not necessarily have to have a pivoting connection.

In the embodiment of FIG. 18B, the anterior effector 448 is configured to engage an anterior side of a rib. This should be interpreted as including, but not necessarily limited to, situations where the anterior effector 448 is in direct or indirect contact with the anterior side of the rib. In some situations, the anterior effector 448 may contact a portion of a rib retractor which is engaging the rib.

The surgical rib cutter 438 also has a posterior arm unit 454 which is configured to engage a posterior side of the same rib. The posterior arm unit 454 includes a posterior arm 456 and a posterior effector 458. In the embodiment of FIG. 18B, the posterior effector 458 comprises a cutting wedge 460. The geometry of the illustrated cutting wedge 460 is merely one example of a suitable wedge. Those skilled in the art will understand that a variety of wedge shapes may be used, including, but not limited to, those with pointed tips, rounded tips, blunted tips, chiseled tips, square tips, smooth edges, or serrated edges. The posterior arm 456 may have a clearance bend 462 in order to allow the cutter 438 to be positioned around one or more portions of a rib retractor, while that rib retractor is in use. The cutting wedge 460 will have a shape which will encourage a rib under tension to form a green stick break in the vicinity of where the cutting wedge is pressed against the rib. As previously noted, examples of this will be discussed in more detail below, with respect to FIGS. 20A-20D.

In this embodiment, the posterior arm 456 and the posterior effector 458 are separate pieces pivotably held together by a pivot pin 464. In other embodiments, the posterior arm 456 and the posterior effector 458 may be formed as continuous piece. For embodiments where the posterior arm 456 and the posterior effector 458 are separate pieces, the posterior arm 456 and the posterior effector 458 do not necessarily have to have a pivoting connection.

The surgical rib cutter 438 also has an actuator 466 movable relative to the housing 440 and operationally coupled, in this embodiment, to the anterior arm unit 444. In this embodiment, the actuator 466 includes a drive screw 468 and a knob 470 coupled to the drive screw 468 for turning the drive screw 468. The anterior arm 446 of the anterior arm unit 444 has a threaded portion 472 which corresponds to the threads on the drive screw 468. As the knob 470 is turned in a first direction, the drive screw 468 is rotated in the same first direction, and the threaded portion 472 of the anterior arm 446 will move down the drive screw 468 in a generally posterior direction 474. FIGS. 20C-20D will later illustrate how this can be useful when paired with a rib retractor.

In the embodiment of FIG. 18B, the anterior arm 446 is a mobile arm movably coupled to the actuator 466 (via the drive screw 468), while the posterior arm 456 is a fixed arm coupled to the housing 440. Other embodiments may have different configurations, as will be discussed in later examples.

Figure 19:
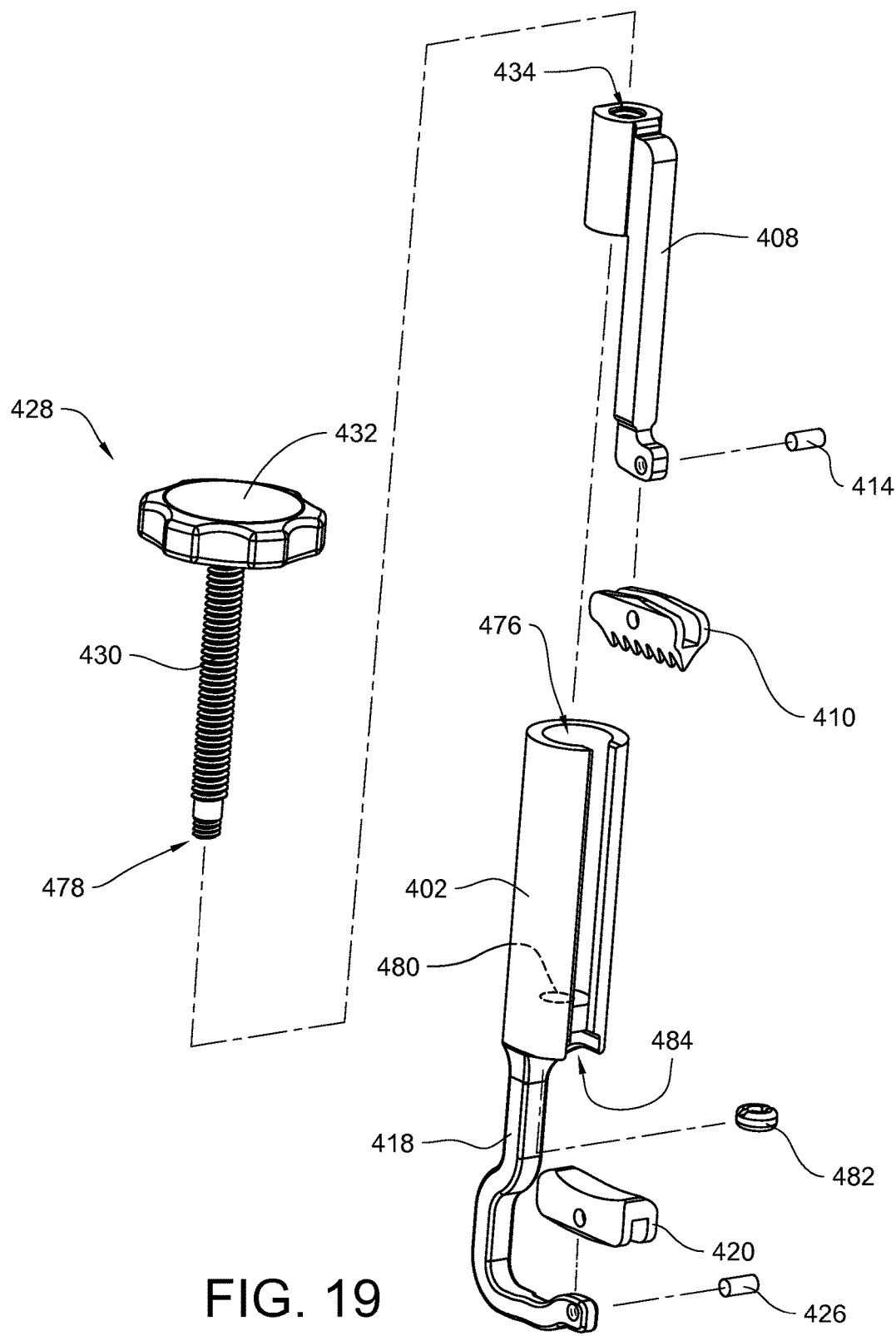
FIG. 19 is an exploded perspective view of the rib cutter of FIG. 18A.

FIG. 19 is an exploded perspective view of the surgical rib cutter of FIG. 18A, the elements of which have been discussed above. As discussed previously, in this embodiment, the actuator 428 includes a knob 432 and a drive screw 430. The drive screw 430 may be threaded into the corresponding threaded portion 434 of the anterior arm 408. This assembly can be dropped into an opening 476 in a first end of the housing 402. The end of the drive screw 478 opposite the knob 432 may be passed through a corresponding opening 480 in the second end of the housing 402. The end of the drive screw 478 may have a smaller diameter than the drive screw 430 so that it can act in conjunction with the corresponding opening 480 in the housing 402 to help stabilize the drive screw 430 in the housing 402. The end of the drive screw 478 may be threaded to engage a round nut 482 which sits inside a recess 484 (not visible in this view) in the bottom of the housing 402. The posterior arm 418 is a continuous extension of the housing 402 in this embodiment. A first pin 414 is used to couple the anterior effector 410 to the anterior arm 408. Similarly, a second pin 426 is used to couple the posterior effector 420 to the posterior arm 418.

FIGS. 20A and 20B demonstrate the rib cutter 400 from FIG. 18A being used in conjunction with an embodiment of a rib retractor 66, the features of which have been discussed above. The ribs 138, 140 are engaged by the posterior strut 90 and the anterior strut 76, respectively, of the retractor 66. As a result, in addition to other possible directional components, the rib 138 is being pushed in a generally posterior direction 486. Similarly, in addition to other possible directional components, the rib 140 is being pulled in a generally anterior direction 488. The rib cutter 400 has been positioned around the rib 140 (the clearance bend 424 facilitating positioning despite the presence of the anterior retractor strut 76) so that the supporting pad 422 of the posterior effector 420 is aligned for engagement with the posterior side of the rib 140. In some embodiments, this engagement may be directly with the posterior side of the rib 140. In other embodiments, this engagement may be indirect, for example, in situations where the supporting pad 422 is positioned against the strut 76 which is pulling on the rib 140. The cutting wedge 412 of the anterior effector 410 is aligned for engagement with the anterior side of the rib 140. Preferably, this alignment is at a point of highest tension on the outer bend of the rib 140, however, other positions could be used.

As illustrated in FIG. 20B, the knob 432 is rotated to cause relative movement between the posterior effector 420 and the anterior effector 410 such that they move towards each other. The cutting wedge 412 will contact the rib 140 as the supporting pad 422 provides a backstop. As the knob 432 is further turned, the cutting wedge 412 will create a line of pressure against the portion of the rib 140 which is under tension, causing a green stick break 490 to form on the anterior side of the rib 140 near to the location of the cutting wedge 412.

FIGS. 20C and 20D demonstrate the rib cutter 438 from FIG. 18B being used in conjunction with an embodiment of a rib retractor 66, the features of which have been discussed above. The ribs 138, 140 are engaged by the posterior strut 90 and the anterior strut 76, respectively, of the retractor 66. As a result, in addition to other possible directional components, the rib 138 is being pushed in a generally posterior direction 486. Similarly, in addition to other possible directional components, the rib 140 is being pulled in a generally anterior direction 488. The rib cutter 438 has been positioned around the rib 138 (the clearance bend 462 facilitating positioning despite the presence of the posterior retractor strut 90) so that the supporting pad 450 of the anterior effector 448 is aligned for engagement with the anterior side of the rib 138. In some embodiments, this engagement may be directly with the anterior side of the rib 138. In other embodiments, this engagement may be indirect, for example, in situations where the supporting pad 450 is positioned against the strut 90 which is pushing on the rib 138. The cutting wedge 460 of the posterior effector 458 is aligned for engagement with the posterior side of the rib 138. Preferably, this alignment is at a point of highest tension on the outer bend of the rib 138, however, other positions could be used.

As illustrated in FIG. 20D, the knob 470 is rotated to cause relative movement between the posterior effector 458 and the anterior effector 448 such that they move towards each other. The cutting wedge 460 will contact the rib 138 as the supporting pad 450 provides a backstop. As the knob 470 is further turned, the cutting wedge 460 will create a line of pressure against the portion of the rib 138 which is under tension, causing a green stick break 492 to form on the posterior side of the rib 138 near to the location of the cutting wedge 460.

In the previous rib cutter embodiments, the posterior arm of the rib cutter was fixedly coupled to the housing, while the anterior arm was movably coupled to a drive screw. FIG. 21, on the other hand, illustrates an embodiment of a surgical rib cutter 494, in partial cross-sectional view, where the anterior arm 496 is fixedly coupled to the housing 498. The housing 498 defines a guide slot 500. The cutter 494 has an actuator 502 comprising a drive screw 504 and a knob 506 coupled to the drive screw 504 for turning the drive screw 504. The drive screw 504 is operationally coupled to a threaded portion 508 of the posterior arm 510. Like some of the previous embodiments, the posterior arm 510 comprises a clearance bend 512. The posterior arm 510 is coupled to a posterior effector 514. The posterior effector 514 is illustrated in this embodiment as comprising a supporting pad 516. In other embodiments, the posterior effector might comprise a wedge cutter instead. The anterior arm 496 is coupled to an anterior effector 518 which, in this example, comprises a wedge cutter 520. In other embodiments, the anterior effector 518 might comprise a supporting pad, instead. When the knob 506 is turned, the posterior arm 510 may be drawn towards the knob 506. Since the anterior arm 496 is fixed to the housing 498, this creates a relative movement between the anterior and posterior arm units.

FIG. 22 illustrates a further embodiment of a surgical rib cutter 522 in partial cross-sectional view front view. The rib cutter 522 has a housing 524 which defines a guide slot 526. The cutter 522 has an actuator 528 comprising a drive screw 530 and a knob 532 coupled to the drive screw 530 for turning the drive screw 530. In this embodiment, the drive screw 530 has an anterior threaded portion 534 and a posterior threaded portion 536. The threads of the anterior and posterior threaded portions 534, 536 are oriented in opposite directions.

In this embodiment, the anterior threaded portion 534 of the drive screw 530 is operationally coupled to a threaded portion 538 of an anterior arm 540. Similarly, the posterior threaded portion 536 of the drive screw 530 is operationally coupled to a threaded portion 542 of a posterior arm 544. The anterior arm 540 is coupled to an anterior effector 546, which comprises a cutting wedge 548 in this embodiment. The posterior arm 544 is coupled to a posterior effector 550, which comprises a supporting pad 552 in this embodiment. When the knob 532 is turned, the anterior arm 540 and the posterior arm 544 can move towards each other or away from each other, depending on the direction of knob 532 rotation.

Referring temporarily back to FIGS. 18A and 18B, it can be seen that two different configurations of surgical rib cutters 400 and 438 may be needed to create a green stick break, depending on whether an anterior green stick break or a posterior green stick break is desired. In some scenarios, this can mean that two different rib cutter devices will need to be available to a surgeon during an operation. Those skilled in the art, however, will see that other embodiments of a surgical rib cutter may be configured so that the anterior and posterior effectors may be swapped. This would enable a single rib cutter to be used to create anterior or posterior green stick breaks, depending on how the effectors are installed.

Figure 23:
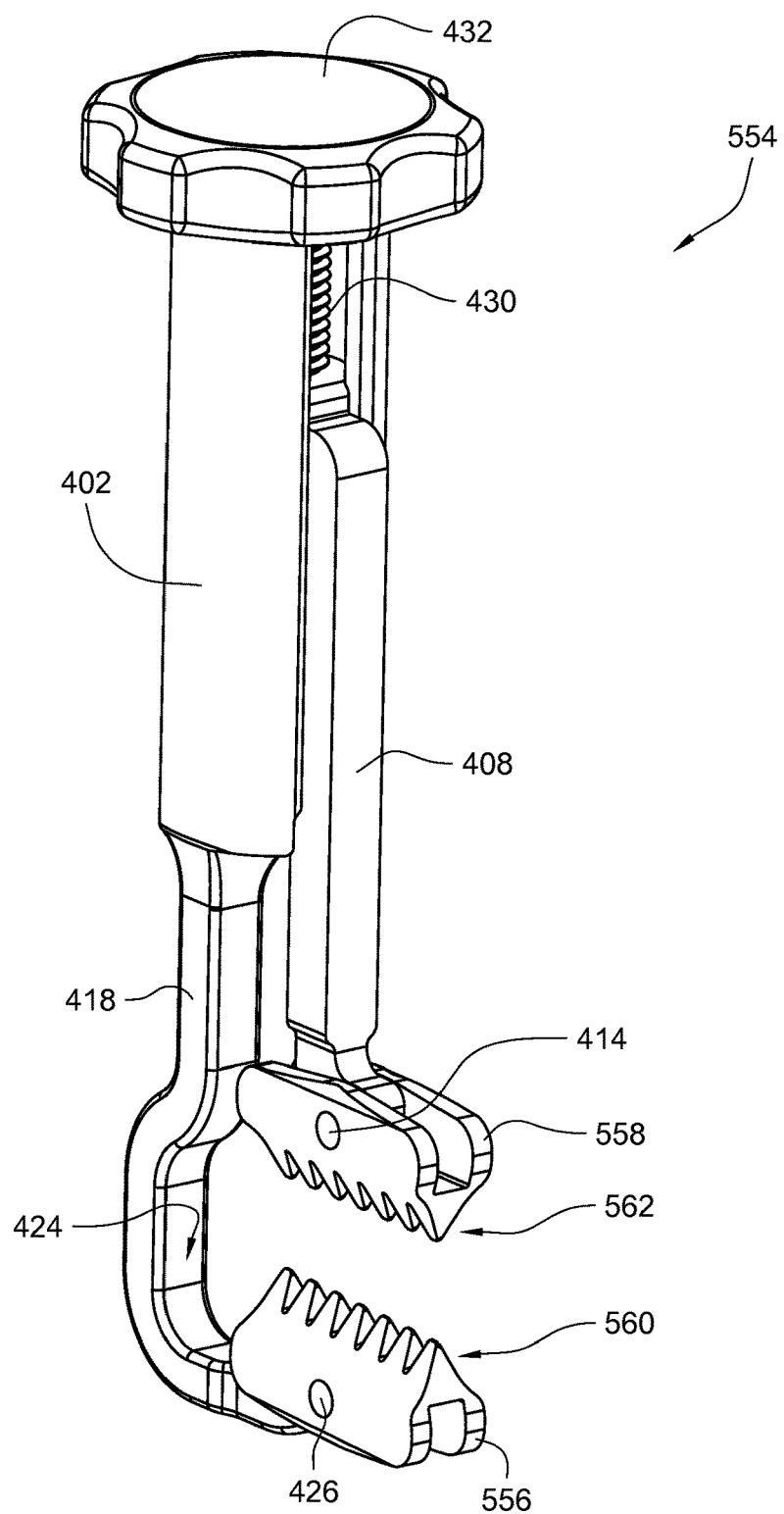
FIG. 23 is perspective view of another embodiment of a rib cutter for inducing a "green stick break" in a rib.

As noted above, the rib cutter's effector which comprises a supporting pad is being used as a backstop, rather than as a cutting surface. As also noted, however, the effector acting as a supporting pad may not always be directly in contact with the rib it is backstopping. As just one example, if the rib retractor being used with the cutter has a nearly continuous set of strut fingers, then the rib cutter's effector which is acting as a supporting pad will be directly contacting the retractor, and not the rib, on the side opposite the effector intended to create the green stick break. Such a situation makes possible a further embodiment of a surgical rib cutter 554 as illustrated in FIG. 23. In this embodiment, both the posterior effector 556 and the anterior effector 558 of the rib cutter 554 comprise cutting wedges 560 and 562, respectively. Either effector 556, 558 may be used to contact a first side of a rib in a location intended to create a green stick break, while the other effector would contact the fingers of the rib retractor. The fingers of the rib retractor would protect the second side of the rib from the cutting wedge on that side of the rib. The other elements of the rib cutter 554 are similar to the embodiments above and have been discussed previously.

Various advantages of a surgical rib cutter have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. As one example, although a knob and drive screw were used as examples of actuators herein, it should be apparent to those skilled in the art that other types of actuators may be used to create a similar relative movement between the posterior and anterior arm units. As some non-limiting examples, other actuators may include, but are not limited to, a ratchet mechanism, a geared mechanism, a levered mechanism, a motorized mechanism, or any combination and/or plurality thereof. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A surgical rib cutter, comprising:
a housing defining one or more guide slots;
an anterior arm unit comprising an anterior effector and an anterior arm configured to interact with an anterior side of a rib, wherein the anterior effector is pivotably coupled to the anterior arm;
a posterior arm unit comprising a posterior effector and a posterior arm configured to interact with a posterior side of said rib, wherein the posterior effector is pivotably coupled to the posterior arm;
wherein at least one of the anterior and posterior arm units further comprises a supporting pad configured to interact with the rib in opposition to a cutting wedge; and
an actuator movable relative to the housing and operationally coupled to at least one of the anterior and posterior arm units to move said at least one of the anterior and posterior arm units within at least one of the one or more guide slots to create a relative movement between the anterior and posterior arm units, said relative movement causing one of the anterior effector or the posterior effector to create a green stick break in said rib.

2. The surgical rib cutter of claim 1, wherein:
the anterior effector comprises the cutting wedge; and
the posterior effector comprises the supporting pad.

3. The surgical rib cutter of claim 1, wherein:
the anterior effector comprises the supporting pad; and
the posterior effector comprises the cutting wedge.

4. The surgical rib cutter of claim 1, wherein the housing comprises a substantially cylindrical shape.

5. The surgical rib cutter of claim 1, wherein at least one of the one or more guide slots, defined by the housing, is a guide slot substantially parallel to a longitudinal axis of the housing.

6. The surgical rib cutter of claim 1, wherein the anterior arm comprises a mobile arm movably coupled to the actuator.

7. The surgical rib cutter of claim 1, wherein the anterior arm comprises a fixed arm coupled to the housing.

8. The surgical rib cutter of claim 1, wherein the posterior arm comprises a mobile arm movably coupled to the actuator.

9. The surgical rib cutter of claim 1, wherein the posterior arm comprises a fixed arm coupled to the housing.

10. The surgical rib cutter of claim 1, wherein the posterior arm comprises a clearance bend configured to clear a rib retractor to allow the anterior and posterior effectors to interact with the anterior and posterior sides, respectively, of the rib while the rib is being retracted by the rib retractor.

11. The surgical rib cutter of claim 1, wherein the actuator comprises:
a drive screw; and
a knob coupled to the drive screw for turning the drive screw.

12. A surgical rib cutter, comprising:
a) a housing defining one or more guide slots;
b) an anterior arm unit comprising an anterior arm and an anterior effector having a cutting wedge wherein the anterior effector is pivotably coupled to the anterior arm, and configured to interact with an anterior side of a rib;
c) a posterior arm unit comprising:
　1) a posterior effector having a supporting pad and configured to interact with a posterior side of said rib in opposition to the cutting wedge; and
　2) a clearance bend configured to clear a rib retractor to allow the anterior and posterior effectors to interact with the anterior and posterior sides, respectively, of said rib while said rib is being retracted by the rib retractor; and
d) an actuator movable relative to the housing and operationally coupled to at least one of the anterior and posterior arm units to move said at least one of the anterior and posterior arm units within at least one of the one or more guide slots to create a relative movement between the anterior and posterior arm units, said relative movement causing the cutting wedge of the anterior effector to create a green stick break on the anterior side of said rib.

13. A surgical rib cutter, comprising:
a) a housing defining one or more guide slots;
b) an anterior arm unit comprising an anterior arm and an anterior effector having a supporting pad wherein the anterior effector is pivotably coupled to the anterior arm, and configured to interact with an anterior side of a rib in opposition to the cutting wedge;
c) a posterior arm unit comprising:
　1) a posterior effector having a cutting wedge and configured to interact with a posterior side of said rib; and
　2) a clearance bend configured to clear a rib retractor to allow the anterior and posterior effectors to interact with the anterior and posterior sides, respectively, of said rib while said rib is being retracted by the rib retractor; and
d) an actuator movable relative to the housing and operationally coupled to at least one of the anterior and posterior arm units to move said at least one of the anterior and posterior arm units within at least one of the one or more guide slots to create a relative movement between the anterior and posterior arm units, said relative movement causing the cutting wedge of the posterior effector to create a green stick break on the posterior side of said rib.

14. A surgical rib cutter, comprising:
a housing defining one or more guide slots;
an anterior arm unit comprising an anterior effector and an anterior arm configured to interact with an anterior side of a rib, wherein the anterior effector comprises a cutting wedge and is pivotably coupled to the anterior arm;
a posterior arm unit comprising a posterior effector and a posterior arm configured to interact with a posterior side of said rib, wherein the posterior effector comprises a cutting wedge and is pivotably coupled to the posterior arm;
wherein the anterior effector comprises a cutting wedge; and
an actuator movable relative to the housing and operationally coupled to at least one of the anterior and posterior arm units to move said at least one of the anterior and posterior arm units within at least one of the one or more guide slots to create a relative movement between the anterior and posterior arm units, said relative movement causing one of the anterior effector or the posterior effector to create a green stick break in said rib.

* * * * *